United States Patent [19]
Abatjoglou et al.

[11] Patent Number: 5,180,854
[45] Date of Patent: Jan. 19, 1993

[54] PROCESS FOR CATALYST ALDEHYDE PRODUCT SEPARATION

[75] Inventors: Anthony G. Abatjoglou, Charleston; David R. Bryant, So. Charleston; Ronald R. Peterson, St. Albans, all of W. Va.

[73] Assignee: Union Carbide Chemicals & Plastics Technology Corporation, Danbury, Conn.

[21] Appl. No.: 853,009

[22] Filed: Mar. 18, 1992

Related U.S. Application Data

[63] Continuation of Ser. No. 373,206, Jul. 5, 1989, abandoned, which is a continuation-in-part of Ser. No. 218,911, Jul. 14, 1988, abandoned.

[51] Int. Cl.$^5$ .................... C07C 45/50; C07C 45/78
[52] U.S. Cl. .................... 568/454; 568/451; 568/492
[58] Field of Search .................... 568/451, 454, 492

[56] References Cited

U.S. PATENT DOCUMENTS

| | | | |
|---|---|---|---|
| Re. 31,812 | 4/1985 | Kuntz | 568/454 |
| 3,959,385 | 4/1976 | Nienburg et al. | 260/604 HF |
| 4,248,802 | 4/1981 | Kuntz | 568/454 |
| 4,263,449 | 4/1981 | Saito et al. | 560/263 |
| 4,399,312 | 8/1983 | Russell et al. | 568/454 |
| 4,479,012 | 10/1984 | Fischer et al. | 568/492 |
| 4,483,801 | 11/1984 | Sabot | 562/35 |
| 4,483,802 | 11/1984 | Gärtner et al. | 562/35 |
| 4,504,588 | 3/1985 | Gartner et al. | 502/24 |
| 4,523,036 | 5/1985 | Cornils et al. | 568/454 |
| 4,537,997 | 8/1985 | Kojima et al. | 568/454 |
| 4,633,021 | 12/1986 | Hanes | 568/454 |
| 4,678,857 | 7/1987 | Dureanleau et al. | 568/492 |
| 4,716,250 | 12/1987 | Abatjoglou et al. | 568/454 |
| 4,731,485 | 3/1988 | Cornils et al. | 568/454 |
| 4,731,486 | 3/1988 | Abatjoglou | 568/454 |
| 4,740,626 | 4/1988 | Bahrmann et al. | 568/454 |

FOREIGN PATENT DOCUMENTS

| | | | |
|---|---|---|---|
| 1093346 | 11/1960 | Fed. Rep. of Germany | 568/492 |
| 1188068 | 4/1965 | Fed. Rep. of Germany | 568/492 |
| 259194 | 8/1988 | German Democratic Rep. | |
| 0123930 | 9/1981 | Japan | 568/492 |
| 1493154 | 11/1977 | United Kingdom | |

OTHER PUBLICATIONS

"Organic Phosphorus Compounds" vol. 1, (1972), pp 31, 41 & 42, G. M. Kosolapoff & L. Maier; Wiley–Interscience.

U.S. Pending application Ser. No. 437,784, filed Nov. 21, 1989 which is a continuation of Ser. No. 357,611, filed May 25, 1989 which in turn is a continuation of Ser. No. 218,895 filed Jul. 14, 1988.

"Synthesis of Phosphino Alkane Sulfonates and Their Corresponding Sulfonic Acids by Reaction of Alkalimetalphosphides with Sultones" by E. Paetzold et al in the *Journal of Prakt. Chemie*, vol. 329, No. 4, (1987) pp. 725-731 (Article in English).

"Continuous Hydroformylation with Water-Soluble Rodium Catalysts" by H. Bach et al in *International Congress of Catalysis Procedings*, 8th, vol. 5, pp. 417-427 (1984).

*Primary Examiner*—Werren B. Lone
*Attorney, Agent, or Firm*—R. J. Finnegan

[57] ABSTRACT

Process for the separation and recovery of aldehyde product from a non-aqueous hydroformylation reaction product composition comprising the aldehyde product, a rhodium-ionically charged phosphorus ligand complex, a free ionically charged phosphorus ligand and an organic solubilizing agent for said complex and said free ligand via phase separation using added water or both added water and an added non-polar hydrocarbon compounds.

59 Claims, 1 Drawing Sheet

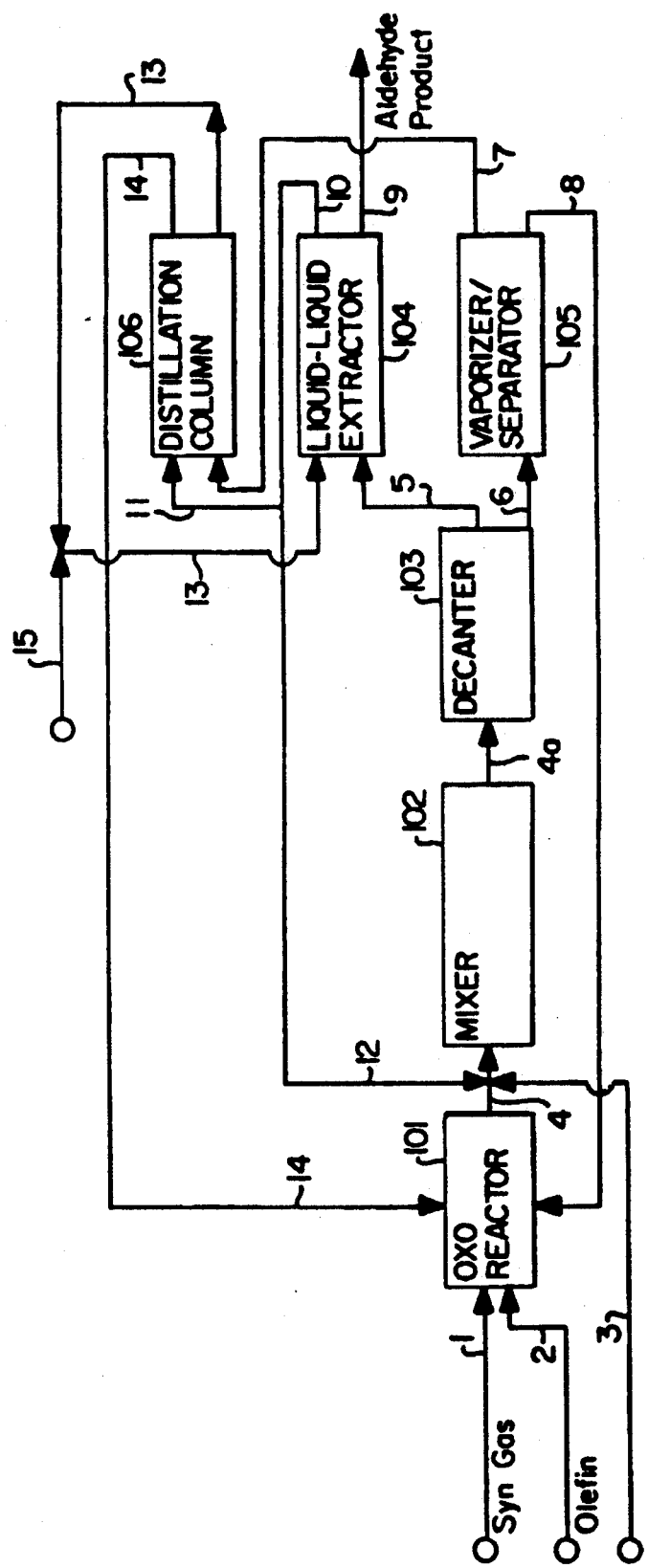

PROCESS FOR CATALYST ALDEHYDE PRODUCT SEPARATION

This application is a continuation of prior U.S. application: Ser. No. 373,206 filing date Jul. 5, 1989 abandoned which is a continuation-in-part of application Ser. No. 218,911 Jul. 14, 1988 abandoned.

This invention relates to the separation and recovery of the aldehyde product from a non-aqueous hydroformylation reaction product composition comprising the aldehyde product, a rhodium-phosphorus ligand complex, free phosphorus ligand and an organic solubilizing agent for said complex and said free ligand, and wherein the phosphorus ligand of said complex and said free phosphorus ligand is an ionically charged phosphorus ligand.

More particularly, this invention relates to the separation and recovery of the aldehyde product from such non-aqueous hydroformylation reaction product compositions by phase separation.

BACKGROUND OF THE ART

The hydroformylation of an olefinic compound with carbon monoxide and hydrogen to produce aldehydes using an organic solubilized rhodium-phosphorus ligand complex catalyst is well known in the art.

For the most part such prior art methods have involved the non-aqueous hydroformylation of an olefin using rhodium-phosphorus ligand complex catalysts wherein the phosphorus ligand is an organophosphine or organophosphite free of an ionic charge, e.g., simple triphenylphosphine. However, while such processes have been very effective in hydroformylating low molecular weight olefins, their use has been found to be curtailed somewhat when hydroformylating high molecular weight olefins due to the difficulty in separating the higher boiling aldehyde products from the rhodium-phosphorus complex containing reaction product composition.

It has been proposed to use aqueous solutions of sulfonated aryl phosphine compounds as the phosphorus ligand, such as the sulfonated triphenylphosphine salts disclosed e.g., in EPC 163234 and U.S. Pat. Nos. 4,248,802, 4,399,312, and the like, as the phosphorus ligand in an aqueous hydroformylation process to facilitate the separation and recovery of the rhodium-phosphorus complex. However, all such prior art methods also involve the employment of a large amount of water to establish a two-phase liquid, non-homogenous hydroformylation reaction medium made up of both an organic phase containing the reaction starting materials and products and an aqueous or water phase containing the catalyst complex and sulfonated phosphine ligands. Moreover, such aqueous or water phase type hydroformylation systems in general require high reactor pressures and/or high metal catalyst concentrations to overcome intrinsically low hydroformylation reaction rates and/or the use of larger and more costly processing apparatus equipment.

It has further been proposed to hydroformylate olefins in a non-aqueous manner employing ionically charged phosphorus ligands and a rhodium-phosphorus ligand complex catalyst such as disclosed e.g., in assignee's U.S. Pat. Nos. 4,731,486 and 4,633,021. However, said U.S. Pat. No. 4,731,486 advocates the use of distillation to separate and recover the aldehyde product, while U.S. Pat. No. 4,633,021 promotes recovery of the aldehyde by extraction with a hydrocarbon solvent and both methods have certain drawbacks. For instance, the higher the molecular weight of the aldehyde product the more difficult distillation becomes due to the higher temperatures required. Moreover, extraction with a hydrocarbon alone is not considered to be a very efficient separation method, since it has been found to extract substantial amounts of the rhodium-phosphorus complex and/or free phosphorus ligand and/or the organic solubilizing agent for said complex and said free ligand that are also present in the reaction product composition in addition to extracting the aldehyde product.

Therefore, there remains a need in the hydroformylation art for a more effective and simple method for efficiently separating higher molecular weight aldehyde products from such non-aqueous hydroformylation reaction product compositions.

DISCLOSURE OF THE INVENTION

It is now been discovered that high molecular weight (e.g., $C_7$ to $C_{31}$) aldehyde products may be readily and easily separated from such non-aqueous hydroformylation reaction product compositions by phase separation brought on by treating said compositions with added water, or added water and an added non-polar hydrocarbon compound. Surprisingly, such treatments have been found to induce excellent overall phase separation or partitioning of all the main components of such hydroformylation reaction product compositions. For instance, said compositions upon having been mixed with added water or added water and an added non-polar hydrocarbon compound have been found to rapidly form two liquid phases, a non-polar phase consisting essentially of the aldehyde products (and the non-polar hydrocarbon when used) and a polar phase consisting essentially of water, the rhodium-phosphorus ligand complex, the free phosphorus ligand, the organic solubilizing agent for said complex and said free ligand. The aldehyde product containing non-polar phase of such types of treatments can then be easily recovered in any conventional manner desired, e.g., by simple decantation, and the rhodium-phosphorus complex containing polar phase, after removal of the water, recycled to the hydroformylation reactor.

Thus, it is an object of this invention to provide a novel process for separating high molecular weight aldehyde products from a non-aqueous hydroformylation reaction product composition that also contains a rhodium-ionically charged phosphorus ligand complex, free ionically charged phosphorus ligand, and an organic solubilizing agent for said complex and said free ligand. Other objects and advantages of this invention will become readily apparent from the following written description and appended claims.

Accordingly, a generic aspect of this invention can be described as a process for separating aldehyde from a non-aqueous hydroformylation reaction product composition comprising aldehyde, a rhodium-phosphorus ligand complex, free phosphorus ligand, and an organic solubilizing agent for said complex and said free ligand, wherein the phosphorus ligand of said complex and said free phosphorus ligand is an ionically charged phosphorus ligand, as further defined herein below, said process comprising (1) mixing said non-aqueous composition with from about 2 to about 60 percent by weight of added water and from 0 to about 60 percent by weight of an added non-polar hydrocarbon compound, said amounts of added water and added non-polar hydrocarbon compound being based on the total weight of said liquid non-aqueous composition, and by phase separation forming a non-polar phase consisting essentially of aldehyde and the added non-polar hydrocarbon compound when employed, and a liquid polar phase consisting essentially of the added water, the rhodium-phosphorus complex, the free phosphorus ligand and the organic solublilizing agent for said complex and said free ligand; with the proviso that the amount of added water employed or the sum amount of added water and added non-polar hydrocarbon employed is at least sufficient to provide phase separation of at least about 70 weight percent of the aldehyde contained in said non-aqueous composition from at least about 95 weight percent of the rhodium-phosphorus complex calculated as rhodium metal also contained in said non-aqueous composition, and (2) recovering said non-polar phase from said polar phase.

BRIEF DESCRIPTION OF THE DRAWING

The Figure is as a schematic block flow diagram of the advantageous use of this invention as it pertains to the recovery of aldehyde from a continuous liquid rhodium catalyst recycle, non-aqueous hydroformylation process.

On the drawing (FIG.), like numbers are utilized to identify like parts.

DESCRIPTION OF THE PREFERRED EMBODIMENTS

As seen discussed above this invention is directed to separating the aldehyde product from a non-aqueous hydroformylation reaction product composition via phase separation. Thus the term "non-aqueous hydroformylation reaction product composition" as employed herein means any non-aqueous composition comprising aldehyde, a rhodium-phosphorus ligand complex, free phosphorus ligand, and an organic solubilizing agent for said complex and said free ligand, wherein the phosphorus ligand of said complex and said free phosphorus ligand is an ionically charged phosphorus ligand. As pointed out above non-aqueous methods for hydroformylating olefins to produce aldehydes with a rhodium-phosphorus ligand complex catalyst in the presence of free phosphorus ligand and an organic solubilizing agent for said catalyst and said free ligand, wherein the phosphorus ligand of said catalyst and said free ligand is an ionically charged phosphorus ligand, have heretofore been proposed. Thus it should be clear that the non-aqueous hydroformylation reaction product compositions employable as the starting material of the phase separation procedure of this invention may be derived from any such corresponding non-aqueous hydroformylation process. Moreover, the particular non-aqueous hydroformylation process, as well as the reaction conditions of such processes, are not critical features of the present invention, since such serve only as a means for furnishing the non-aqueous compositions employable as the starting material of the phase separation procedure of this invention.

Accordingly the non-aqueous hydroformylation reaction product composition starting materials employable herein contain at least some amount of four different main ingredients or components, i.e., the aldehyde product, a rhodium-phosphorus ligand complex, free phosphorus ligand, and an organic solubilizing agent for said complex and said free ligand, said ingredients corresponding to those employed and/or produced by the non-aqueous hydroformylation process from whence the non-aqueous hydroformylation reaction product composition starting material may be derived. Of course it is to be further understood that the non-aqueous hydroformylation reaction product compositions employable herein can and normally will contain minor amounts of additional ingredients such as those which have either been deliberately employed in the non-aqueous hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, and high boiling liquid aldehyde condensation by-products, as well as other inert co-solvent type materials or hydrocarbon additives, if employed.

As noted, the non-aqueous hydroformylation reaction product compositions employable herein contain both a rhodium-phosphorus ligand complex and free phosphorus ligand. By "free ligand" is meant phosphorus ligand that is not complexed with (tied to or bound to) the rhodium atom of the complex. Moreover the term "non-aqueous" as employed herein with regard to the hydroformylation process from whence the non-aqueous hydroformylation reaction product composition starting materials of this invention may be derived means that the hydroformylation reaction is conducted, in the absence or essential absence of water, which is to say that any water, if present at all, in the hydroformylation reaction medium, is not present in an amount sufficient to cause either the hydroformylation reaction or said medium to be considered as encompassing a separate aqueous or water phase or layer in addition to an organic phase. Similarly, the term "non-aqueous" as employed herein with regard to the hydroformylation reaction product composition starting materials of this invention means that said reaction product composition starting materials are also free to essentially free of water, which is to say that any water, if present at all in said hydroformylation reaction product composition starting materials (prior to course to any deliberate addition of water as called for by the subject invention) is not present in an amount sufficient to cause the hydroformylation reaction product composition starting material to be considered as encompassing a separate aqueous or water phase or layer in addition to an organic phase. The high molecular weight aldehyde products contained in the non-aqueous hydroformylation reaction product compositions employable in this invention and which can be removed therefrom by the phase separation process of this invention are those aldehydes containing from 7 to 31 carbon atoms. Such aldehydes then may encompass the corresponding hydroformylation aldehyde products obtained upon hydroformylating olefinic compounds containing from 6 to 30 carbon atoms which can be terminally or internally unsaturated and be of straight-chain, branched-chain or cyclic structures and which further may contain one or more ethylenic unsaturated groups. Moreover such olefinic materials, and consequently their corresponding hydroformylation aldehyde products, may contain one or more groups or substituents which do not unduly adversely interfere with the hydroformylation process and phase separation process of this invention, such as carbonyl, carbonyloxy, oxy, hydroxy, oxycarbonyl, halogen, alkoxy, aryl, haloalkyl, and the like. Thus, for instance, the aldehyde products may correspond to those obtained upon hydroformylating alpha olefins, internal olefins, alkyl alkenoates, alkenyl alkanoates, alkenyl alkyl ethers, alkenols, and the like, e.g., 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 1-docosene, 1-tetracosene, 1-hexacosene, 1-octacosene, 1-triacontene, 2-octene, styrene, 3-phenyl-1-propene, 1,4-hexadiene, 1,7-octadiene, 3-cyclohexyl-1-butene, hex-1-en-4-ol, oct-1-en-4-ol, allyl propionate, allyl butyrate, n-propyl-7-ocetanoate, 4-methyl styrene, 4-isopropyl styrene, 4-tert-butyl styrene, alpha-methyl styrene, 4-tert-butyl-alpha-methyl styrene, 1,3-diisopropenyl-benzene, eugenol, iso-eugenol, safrole, iso-safrole, anethol, 4-allylanisole, indene, limonene, beta-pinene, dicyclopentadiene, cyclooctadiene, camphene, linalool, and the like.

Illustrative aldehydes products thus include heptanal, 2-methyl-1-hexanal, octanal, 2-methyl-1-heptanal, nonanal, 2-methyl-1-octanal, 2-ethyl-1-heptanal, 3-propyl-1-hexanal, decanal, 2-methyl-1-nonanal, undecanal, 2-methyl-1-decanal, dodecanal, 2-methyl-1-undecanal, tridecanal, 2-methyl-1-dodecanal, tetradecanal, 2-methyl-1-tridecanal, 2-ethyl-1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonadecanal, 2-methyl-1-octadecanal, 2-ethyl-1-heptadecanal, 3-propyl-1-hexadecanal, eicosanal, 2-methyl-1-nonadecanal, heneicosanal, 2-methyl-1-eicosanal, tricosanal, 2-methyl-1-docosanal, tetracosanal, 2-methyl-1-tricosanal, pentacosanal, 2-methyl-1-tetracosanal, 2-ethyl-1-tricosanal, 3-propyl-1-docosanal, heptacosanal, 2-methyl-1-octacosanal, nonacosanal, 2-methyl-1-octacosanal, hentriacontanal, 2-methyl-1-triacontanal.

Of course it is understood that the aldehyde product of an alpha olefin will normally be a mixture of the normal straight chain aldehyde and its branched chain aldehyde isomer obtained upon hydroformylating said olefin. Moreover mixtures of totally different aldehyde products can be present in the non-aqueous hydroformylation product compositions employable in this invention, e.g., when such compositions are derived from a process that hydroformylated mixtures of totally different olefinic compounds, such as e.g., mixtures of alpha olefins and internal olefins or mixtures of two different alpha olefins. The preferred aldehyde products present in the hydroformylation reaction product compositions employable in this invention are those containing from 7 to 25 carbon atoms, especially those derived from hydroformylating alpha olefins containing from 6 to 24 carbon atoms. It is of course to be further understood that some commercial olefins may also contain minor amounts of corresponding internal olefins and/or their corresponding saturated hydrocarbons and that such commercial olefins need not necessarily be purified from same prior to being hydroformylated to provide the non-aqueous hydroformylation reaction product compositions employable in this invention.

The amount of aldehyde product present in the non-aqueous hydroformylation reaction product compositions employable as the starting materials of this invention may range from about 10 percent by weight or lower to about 90 percent or higher of the non-aqueous hydroformylation reaction product composition. Such amounts are not narrowly critical and will of course in general merely be dependent upon the particular reaction conditions and efficiency of the non-aqueous hydroformylation process from whence the non-aqueous hydroformylation reaction product composition may be derived. In general, preferred non-aqueous hydroformylation processes are those capable of producing a hydroformylation reaction medium containing from about 20 to about 80 percent by weight of aldehyde product. Correspondingly, the amount of aldehyde product present in the non-aqueous hydroformylation reaction product compositions employable in this invention may be preferably in the range of from about 20 to about 80 percent by weight of the non-aqueous hydroformylation reaction product composition.

The ionically charged phosphorus ligands employable in this invention as both the phosphorus ligand of the rhodium-phosphorus complex and free phosphorus ligand are monosulfonated tertiary phosphine metal salts having the general formula

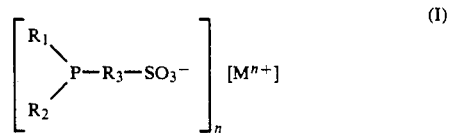

(I)

wherein $R_1$ and $R_2$ each individually represent a radical containing from 1 to 30 carbon atoms selected from the class consisting of alkyl, aryl, alkaryl, aralkyl and alicyclic radicals and wherein $R_3$ represents a divalent alkylene radical having from 2 to 12, preferably 2 to 5 carbon atoms or a divalent 1,3-phenylene radical, wherein M represents a metal cation selected from the group consisting of alkali and alkaline earth metals, and wherein n has a value of 1 or 2 corresponding to the valence of the particular metal cation represented by M.

Illustrative radicals represented by the $R_1$ and $R_2$ groups in the above monosulfonated tertiary phosphine metal salt ligand formula include monovalent hydrocarbon radicals containing from 1 to 30 carbon atoms, e.g., alkyl radicals including linear or branched, primary, secondary or tertiary alkyl radicals, such as methyl, ethyl, n-propyl, isopropyl, butyl, sec-butyl, t-butyl, t-butylethyl, t-butylpropyl, n-hexyl, amyl, sec-amyl, t-amyl, 2-ethylhexyl, n-octyl, iso-octyl, decyl, dodecyl, octadecyl, eicosyl and the like; aryl radicals such as phenyl, naphthyl, and the like; aralkyl radicals such as benzyl, phenylethyl, and the like; alkaryl radicals such as tolyl, xylyl, and the like; and alicyclic radicals such as cyclopentyl, cyclohexyl, cyclooctyl, cyclohexylethyl, and the like. Moreover, such monovalent hydrocarbon radicals may be substituted with any substitutent that does not unduly adversely effect the desired results of this invention. Illustrative substitutents that may be on the hydrocarbon radicals include for example silyl radicals such as $-Si(R^9)_3$; amino radicals such as $-N(R^9)_2$; acyl radicals such as $-C(O)R^9$, acyloxy radicals such as $-OC(O)R^9$; amido radicals such as $-CON(R^9)_2$ and $-N(R^9)COR^9$; sulfonyl radicals such as $-SO_2R^9$, alkoxy radicals such as $-OR^9$; thionyl radicals such as $-SR^9$, phosphonyl radicals such as $-P(O)(R^9)_2$, as well as, halogen, nitro, cyano, trifluoromethyl, and hydroxy radicals, and the like, wherein each $R^9$ individually represents the same or different substituted or unsubstituted monovalent hydrocarbon radical having the same meaning as defined for $R_1$ and $R_2$ above, with the proviso that in amino substituents such as —N(R⁹)₂, each R⁹ taken together can also represent a divalent bridging group that forms a heterocyclic radical with the nitrogen atom, and in amido substituents such as —C(O)N(R⁹)₂ and —N(R⁹)COR⁹ each R⁹ bonded to N can also be hydrogen. Of course it is to be understood that the $R_1$ and $R_2$ groups in a particular given metal salt ligand may be the same or different.

When $R_3$ in the above formula represents a divalent 1,3-phenylene radical, preferably the monovalent hydrocarbon radicals represented by $R_1$ and $R_2$ are selected from the group consisting of alkyl radicals having from $C_1$ to $C_{20}$ carbon atoms, aryl radicals having from $C_6$ to $C_{12}$ carbon atoms, and alicyclic radicals having from $C_5$ to $C_{12}$ carbon atoms. More preferably the $R_1$ and $R_2$ groups are each individually a branched chain alkyl radical having from 3 to 9 carbon atoms (such as iospropyl, t-butyl, etc.), a phenyl or cyclohexyl radical. Most preferably the $R_1$ and $R_2$ radicals in a given monosulfonated tertiary phosphine metal salt each individually represent a phenyl or cyclohexyl radical, especially phenyl, when $R_3$ is a divalent 1,3-phenylene radical.

When $R_3$ in the above formula represents a divalent alkylene radical, preferably $R_1$ represents an aryl radical having from $C_6$ to $C_{12}$ carbon atoms or an alicyclic radical having from $C_5$ to $C_{12}$ carbon atoms and $R_2$ represents an alkyl radical having from $C_1$ to $C_{20}$ carbon atoms, an aryl radical having from $C_6$ to $C_{12}$ carbon atoms or an alicyclic radical having from $C_5$ to $C_{12}$ carbon atoms. More preferably $R_1$ is a phenyl or cyclohexyl radical and $R_2$ is a branched chain alkyl radical having from 3 to 9 carbon atoms (such as isopropyl, t-butyl, etc.), a phenyl or a cyclohexyl radical. Most preferably the $R_1$ and $R_2$ radicals in a given monosulfonated tertiary phosphine metal salt each individually represent a phenyl or a cyclohexyl radical, especially phenyl, when $R_3$ is a divalent alkylene radical having from 2 to 5 carbon atoms, especially 1,3-propylene or 1,4-butylene.

As noted, M in the monosulfonated tertiary phosphine metal salt ligand formula above, represents a metal cation selected from the group consisting of alkali and alkaline earth metals. Illustrative alkali metals include lithium (Li⁺), sodium (Na⁺), potassium (K⁺), cesium (Cs⁺) and rubidium (Rb⁺), while illustrative alkaline earth metals include calcium (Ca⁺⁺), barium (Ba⁺⁺), magnesium (Mg⁺⁺) and strontium (Sr⁺⁺). Moreover as noted above the by the definition of n, the metal salt ligand may contain one or two monosulfonated tertiary phosphine anion molecules corresponding to the positive valence of the metal cation M.

The more preferred class of monosulfonated tertiary phosphine metal salt ligands employable herein are those wherein $R_3$ represents a divalent 1,3-phenylene radical and have the general formula

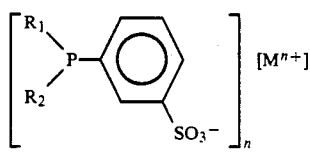

wherein $R_1$, $R_2$, M and n may be the same as defined above, in contrast to those of the class wherein $R_3$ represents a divalent alkylene radical and have the general formula

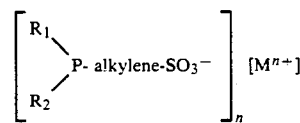

wherein the divalent alkylene radical contains from 2 to 12, preferably 2 to 5 carbon atoms and $R_1$, $R_2$, M and n may be the same as defined above.

Illustrative preferred monosulfonated tertiary phosphine metal salt ligands include (e.g., those having the following general formulas (wherein

represents a phenyl radical; wherein

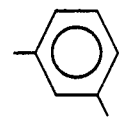

represents a 1,3-phenylene radical and wherein

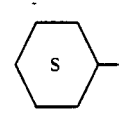

represents a cylcohexyl radical).

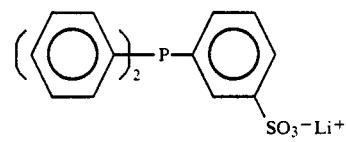

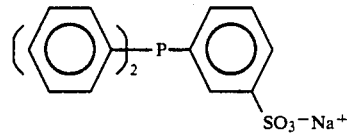

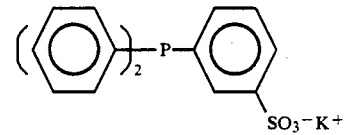

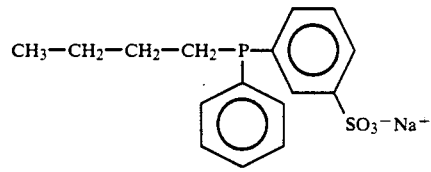

-continued
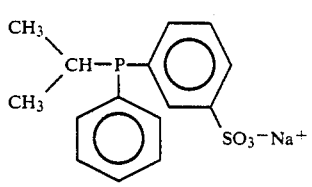
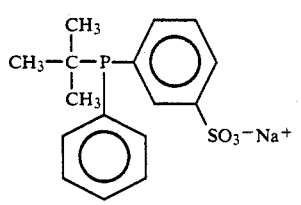
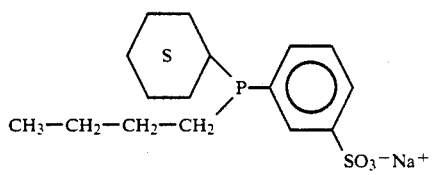
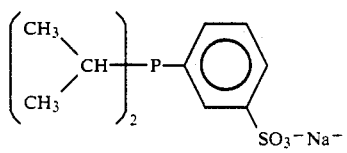
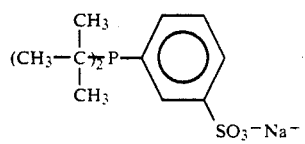
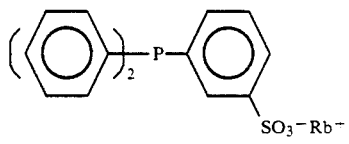
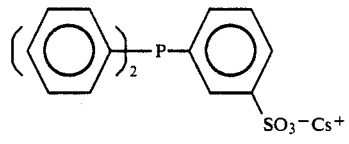
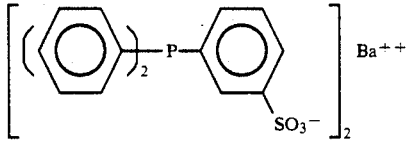
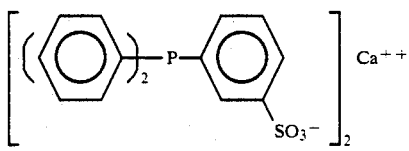
-continued
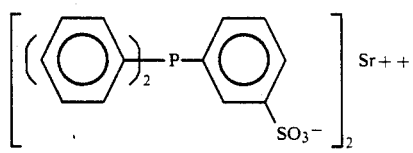
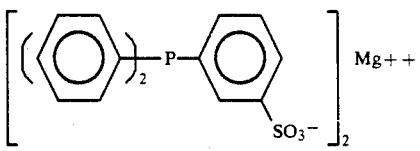
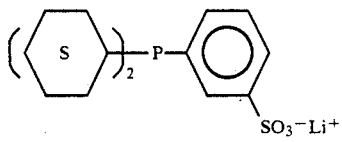
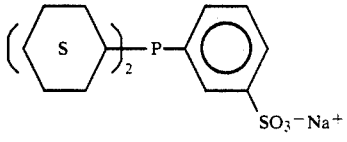
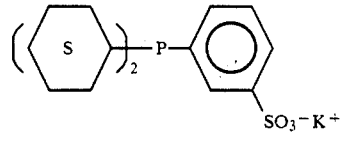
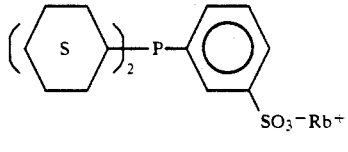
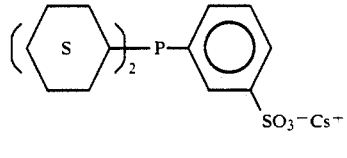
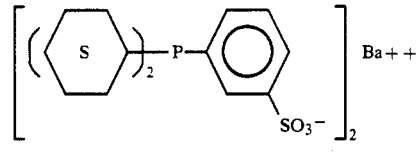
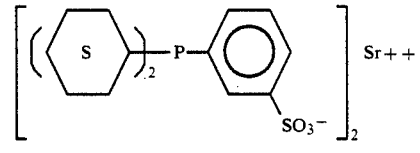
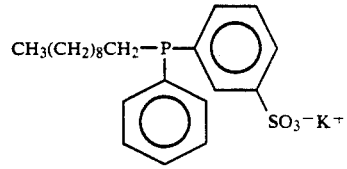

11
-continued
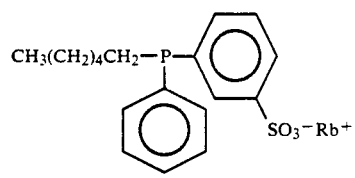
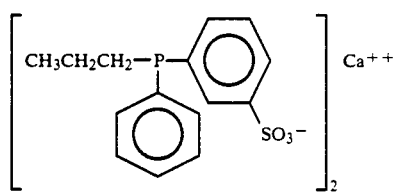
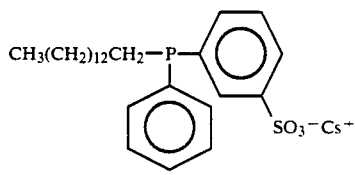
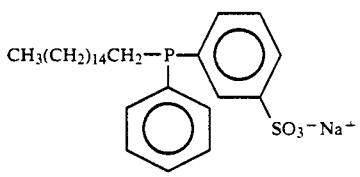
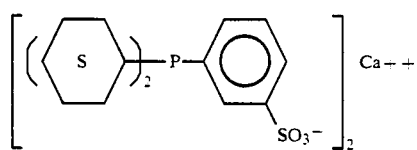
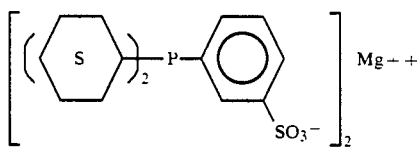
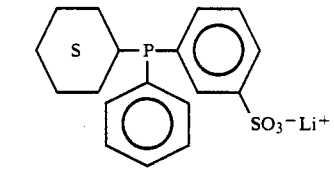
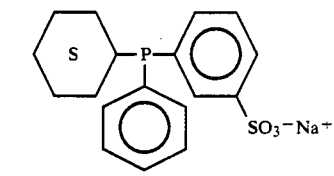
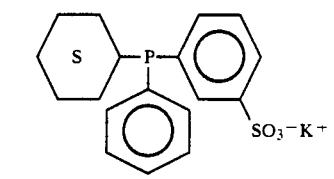
12
-continued
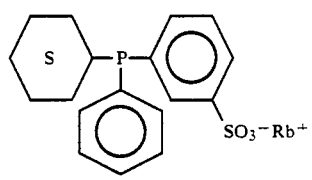
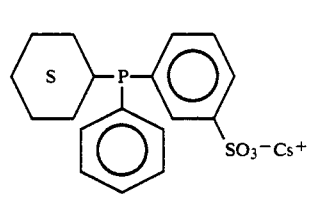
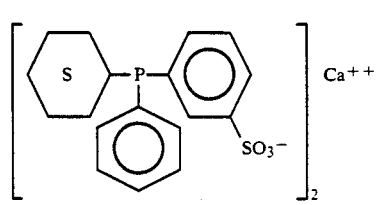
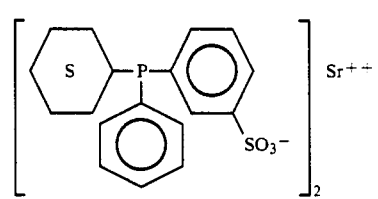
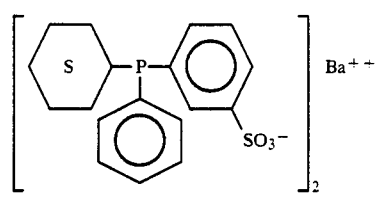
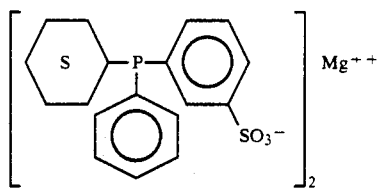
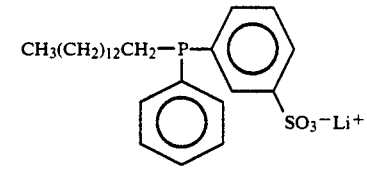
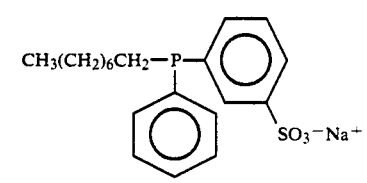

$(CH_3)_2-P-C_3H_6-SO_3^-Na^+$
$(C_2H_5)_2-P-C_3H_6-SO_3^-Na^+$
$(n-C_4H_9)_2-P-C_3H_6-SO_3^-Rb^+$
$(n-C_6H_{13})_2-P-C_3H_6-SO_3^-Na^+$
$(n-C_{10}H_{21})_2-P-C_4H_8-SO_3^-Cs^+$
$[(t-C_4H_9)_2-P-C_4H_8-SO_3^-]_2Ba^{++}$
$[(n-C_3H_7)_2-P-C_3H_6-SO_3^-]_2Ca^{++}$
$[(C_2H_5)_2-P-C_3H_6-SO_3^-]_2Mg^{++}$
$[(n-C_6H_{13})_2-P-C_3H_6-SO_3^-]_2Sr^{++}$
$(iso-C_3H_7)_2-P-C_4H_8-SO_3^-K^+$
$(iso-C_3H_7)_2-P-C_3H_6-SO_3^-Li^+$
$(t-C_4H_9)_2-P-C_3H_6-SO_3^-K^+$ and the like.

Such types of monosulfonated tertiary phosphine metal salts ligands employable in this invention and/or methods for their manufacture are well known or obvious as seen e.g., by the procedures described in "J. Chem. Soc.", pp. 276–288 (1958), U.S. Pat. Nos. 4,483,802, and 4,731,486. For instance such ligands wherein $R_3$ in Formula (I) above is a divalent 1,3-phenylene radical can be prepared by sulfonating a corresponding phenyl containing tertiary phosphine, e.g.,

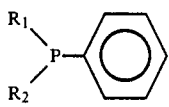

wherein $R_1$ and $R_2$ are the same as defined above with fuming sulfuric acid (oleum) under controlled temperature conditions to form predominately the corresponding protonated monosulfonated phenyl containing tertiary phosphine, e.g.,

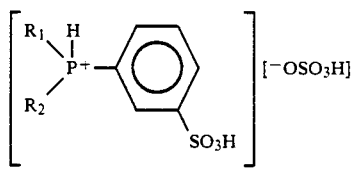

For example, the solid phosphine is added to the fuming sulfuric acid in portions while controlling the temperature below 30° C. and then heated, e.g., to 70°–80° C. until an aliquot from the reaction mixture does not show turbidity. The reaction mixture is then cooled immediately to stop any further sulfonation and without waiting added to water while controlling the temperature below 30° C. and said protonated phosphine salt then neutralized with a corresponding concentrated alkali or alkaline earth metal hydroxide, carbonate or bicarbonate to form the corresponding monosulfonated phenyl containing tertiary phosphine metal salt precipitate, e.g.,

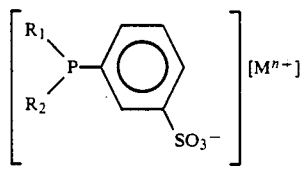

and by product metal sulfate. The tertiary phosphine metal monosulfonate precipitate is then recovered from filtration by extracting it from the metal sulfate with methanol, followed by evaporation of the methanol. The crude tertiary phosphine metal monosulfate precipitate may then be purified, if desired, by dissolving it in a suitable solvent such as water or ethanol and recrystallizing it therefrom. Of course it is understood that $R_1$, $R_2$, M and n in the above formulas are the same as already herein defined above.

Such ligands wherein $R_3$ in Formula (I) above is a divalent alkylene radical may be prepared e.g., by conventional nucleophilic substitution type reactions such as taught in "Organic Phosphorus Compounds" Vol 1, by G. M. Kosolapoff and L. Maier, pp. 41–42 (1972), Wiley-Interscience, for instance by reacting an alkali phosphide, e.g., $R_1R_2PLi$, with a monosulfonated alkyl halide metal salt, e.g., $Cl(CH_2)_xSO_3Li$, to produce the corresponding monosulfonated tertiary phosphine metal salt ligand, e.g., $R_1R_2P(CH_2)_xSO_3Li$, wherein $R_1$ and $R_2$ are the same as defined above and x has a value of 2 to 12. More preferably ligands wherein $R_3$ is a divalent 1,3-propylene or 1,4-butylene radical can be prepared by reacting an alkali phosphide, e.g., $R_1R_2PLi$, with a sultone e.g.,

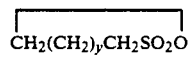

such as gamma-sultone or delta-sultone to produce the corresponding monosulfonated tertiary phosphine metal salt ligand, e.g., $R_1R_2PCH_2(CH_2)_yCH_2SO_3Li$, wherein $R_1$ and $R_2$ are the same as defined above and y has a value of 1 to 2, as shown by the analogous phosphine-sultone reaction disclosed on page 31 of the above mentioned "Organic Phosphorus Compounds" textbook.

Another main component in the non-aqueous hydroformylation reaction product compositions employable in this invention is the rhodium-phosphorus ligand complex which corresponds to the rhodium-phosphorus complex catalyst employed in the non-aqueous hydroformylation reaction process from which said compositions have been derived. Indeed such rhodium-phosphorus ligand complexes present in hydroformylation reaction product compositions are also commonly referred to in the art as rhodium-phosphorus ligand complex catalysts. However, it is to be noted that the successful practice of this invention does not depend and is not predicated on the exact structure of the rhodium-phosphorus complex species present in the non-aqueous hydroformylation reaction product composition starting material of this invention. Such species may be present in their mononuclear, dinuclear and or higher nuclearity forms. Indeed the exact structure is not known. Although it is not intended herein to be bound to any theory or mechanistic discourse, as in the case of the catalytically active rhodium complex species in the non-aqueous hydroformylation process from which the non-aqueous hydroformylation reaction product compositions in this invention may be derived, it is believed that the corresponding complex species in the non-aqueous hydroformylation reaction product composition may in its simplest form consist essentially of rhodium in complex combination with carbon monoxide and monosulfonated tertiary phosphine metal salt ligand. The ultimate composition of the rhodium-phosphorus complex may also contain an additional organic ligand or anion i.e. ligand satisfying the coordination sites or nuclear charge of the rhodium metal as in the case of heretofore conventional hydroformylation rhodium-organophospine catalysts such as e.g., hydrogen and the like. For instance, as in the case of the catalytically active rhodium complex species in the non-aqueous hydroformylation process from which the reaction product compositions of this invention may be derived, wherein the active hydroformylation catalyst species is generally considered to also contain hydrogen directly bonded to the rhodium in view of the hydrogen gas employed in the hydroformylation process, it is likewise considered that the species of the rhodium-phosphorus complex present in the non-aqueous hydroformylation reaction product composition starting materials of this invention may also be complexed with hydrogen in addition to the monosulfonated tertiary phosphine metal salt and carbon monoxide ligands. Of course, it is also possible that rhodium-phosphorus complex species present in the non-aqueous hydroformylation reaction product composition starting materials of this invention may be free of such complexed hydrogen as a result of having been removed from the hydroformylation reaction zone of the hydroformylation reactor.

Thus it is to be understood that the rhodium-phosphorus complex present in the non-aqueous hydroformylation reaction product compositions employed in this invention can be any such complex mixture resulting from the corresponding rhodium-phosphorus complex catalyst present in the hydroformylation reaction medium of the non-aqueous hydroformylation process from whence the particular non-aqueous hydroformylation reaction product composition employable in the process of this invention may be derived. Rhodium-phosphorus complex hydroformylation catalysts may be formed by methods known in the art, for instance preformed rhodium (hydrido) carbonyl monosulfated tertiary phosphine metal salt ligand complex catalysts may be prepared and introduced with a solubilizing agent if necessary into the reaction medium of a non-aqueous hydroformylation process. More commonly the rhodium-monosulfonated tertiary phosphine metal salt ligand complex catalysts of the non-aqueous hydroformylation process are derived from a metal catalyst precursor, such as rhodium dicarbonyl acetylacetonate, $Rh_2O_3$, $R_4(CO)_{12}$, $Rh_6(CO)_{16}$, $Rh(NO_3)_3$, and the like, which may be introduced along with monosulfonated tertiary phosphine metal salt ligand and an added organic solubilizing agent, as defined herein, if necessary for the in situ formation of the active hydroformylation catalyst. A preferred rhodium complex precursor comprises rhodium carbonyl monosulfonated tertiary phosphine metal salt acetylacetonate. In a preferred embodiment a rhodium carbonyl monosulfonated tertiary phosphine metal salt acetylacetonate precursor is introduced into the hydroformylation reactor along with excess free monosulfonated tertiary phosphine metal salt ligand and an added organic solubilizing agent as defined herein, if necessary, for the in situ formation of the active catalyst. In any event, it is sufficient for the purpose of this invention to understand that carbon monoxide, hydrogen and monosulfonated tertiary phosphine metal salt are all ligands that are capable of being complexed with the rhodium metal and that a rhodium-monosulfonated tertiary phosphine metal salt ligand complex is present in the non-aqueous hydroformylation product reaction compositions starting materials of this invention.

Likewise, it should also be clear that the amount of rhodium-phosphorus complex present in a given non-aqueous hydroformylation reaction product composition starting material of this invention will in general correspond to that amount of the corresponding complex catalyst present in the hydroformylation reaction medium of the non-aqueous hydroformylation process from which said non-aqueous hydroformylation reaction product composition may be derived. For instance, since the amount of rhodium-phosphorus complex catalyst present in the hydroformylation reaction medium need only be that minimum amount necessary to provide the rhodium metal concentration desired to be employed and which will furnish the basis for at least that catalytic amount of rhodium necessary to catalyze the hydroformylation process, the amount of rhodium-phosphorus complex present in a given non-aqueous hydroformylation reaction product composition starting material of this invention need only be that amount corresponding to such a minimum amount as just defined. In general, the amount of rhodium-phosphorus complex catalyst present in the hydroformylation reaction medium of a given hydroformylation process is expressed in terms of the amount of rhodium present calculated as rhodium metal, e.g. rhodium concentrations in the range of from about 10 ppm to about 1000 ppm, and preferably from about 10 to 800 ppm, of rhodium calculated as rhodium metal should be sufficient for most hydroformylation processes. Accordingly, the amount of rhodium-phosphorus complex present in a given non-aqueous hydroformylation reaction product composition starting material of this invention may be expressed in the same way and may correspondingly be that amount which will provide a rhodium concentration in the range of from about 10 ppm to about 1000 ppm, preferably that 10 ppm to about 800 ppm, of rhodium calculated as rhodium metal.

As noted above the monosulfonated tertiary phosphine metal salt ligands defined herein are employed in this invention as both the phosphorus ligand of the rhodium-phosphorus ligand complex, as well as, the free phosphorus ligand that is also present in the non-aqueous hydroformylation reaction product composition starting materials employable in this invention. In a given situation such rhodium-phosphorus complexes and free phosphorus ligands of course will correspond to those employed in the non-aqueous hydroformylation process from which said compositions may be derived. In addition, it is to be understood that while the phosphorus ligand of the rhodium-monosulfonated tertiary phosphine metal salt ligand complex and free monosulfonated tertiary phosphine metal salt ligand present in the reaction medium of a given non-aqueous hydroformylation process and its corresponding reaction product composition are normally the same, different monosulfonated tertiary phosphine metal salt ligands, as well as, mixtures of two or more different monosulfonated tertiary phosphine metal salt ligands may be employed for each individual purpose, if desired. As in the case with the amounts of rhodium-phosphorus ligand complex catalyst employed, the amount of free phosphorus ligand present in a given non-aqueous hydroformylation reaction product composition starting material of this invention will in general correspond to that amount of corresponding free phosphorus ligand present in the hydroformylation reaction medium of the non-aqueous hydroformylation process from which said non-aqueous hydroformylation product composition may be derived. For instance, since the hydroformylation process may be carried out in any excess amount of free phosphorus ligand desired, e.g., at least one mole of free monosulfonated tertiary phosphine metal salt ligand per mole of rhodium present in the reaction medium, the amount of free phosphorus ligand present in a given non-aqueous hydroformylation reaction product composition starting material of this invention can also be any corresponding excess amount, e.g., at least one mole of free monosulfonated tertiary phosphine metal salt ligand per mole of rhodium metal present in the non-aqueous hydroformylation reaction product composition. In general amounts of free phosphorus ligand of from about 2 to about 300, and preferably from about 5 to about 200 moles per mole of rhodium metal present in the non-aqueous reaction medium should be suitable for most hydroformylation processes. Accordingly, the amount of free phosphorus ligand in the non-aqueous hydroformylation reaction product composition starting materials of this invention may in general also be from about 2 to about 300, and preferably from about 5 to about 200 moles per mole of rhodium metal present in the non-aqueous hydroformylation reaction product composition.

Preferably the subject process of this invention is one in which the aldehyde product is also highly phase separated from the free phosphorus ligand in addition to the rhodium-phosphorus complex. Accordingly more preferably the subject process of this invention is one in which the amount of added water employed or the sum amount of added water and added non-polar hydrocarbon employed and referred to in the above proviso clause is at least sufficient to provide phase separation of at least about 70 weight percent of the aldehyde contained in the non-aqueous hydroformylation reaction product composition starting material from at least about 95 weight percent of the rhodium-phosphorus complex calculated as rhodium metal and at least about 95 weight percent of the free phosphorus ligand also contained in said non-aqueous composition.

The non-aqueous hydroformylation reaction product composition starting materials employable in this invention also contain an organic solubilizing agent corresponding to that employed for solubilizing the rhodium-phosphorus complex catalyst and free phosphorus ligand in the reaction medium of the non-aqueous hydroformylation process from which said compositions may be derived. The added organic solubilizing agents employable in such non-aqueous hydroformylation processes and present in the non-aqueous hydroformylation reaction product composition starting materials of this invention may be polar organic liquids having a molecular weight of less than 250 and a Hildebrand solubility value of 10 or higher, and mixtures thereof. Illustrative examples of such polar compounds (along with their Hildebrand solubility parameters) include lower alcohols e.g., methanol (12.9), ethanol (11.2), propanol (10.2), isopropanol (10.2) and the like; as well as, nitriles e.g., benzonitrile (10.7), acetonitrile (11.8), propionitrile, and the like; amides e.g., dimethylformamide (11.5), dimethylacetamide, N-methyl pyrrolidone (14.8), N-methyl piperidone, 1,5-dimethyl pyrrolidone,2-pyrrolidone, 2-hydroxyethyl pyrrolidone, N-dodecyl pyrrolidone, N-ethyl pyrrolidone, N-cyclohexyl pyrrolidone, 1,2-di (pyrrolidone) ethane, N,N-dimethylpropionamide, and the like; glycols e.g., ethylene glycol, propylene glycol and the like; polyglycols e.g., diethylene glycol, triethylene glycol, tetraethylene glycol, dipropylene glycol, tripropylene glycol, and the like; sulfoxides e.g., dimethyl sulfoxide (12.8) and the like; sulfones e.g., dimethyl sulfone, sulfolane, and the like; and the like. Hildebrand solubility values are an empirical measure of the relative polarity of an organic compound and are described, e.g., in "Introduction to Modern Liquid Chromatography" by L. R. Snyder and J. J. Kirkland, pp. 215-218 (1974) a Wiley-Interscience publication, (John Wiley & Sons) and "The Solubility of Non-Electrolytes", J. H. Hildebrand and R. L. Scott, pp. 424-434, Dover Publications Inc., New York (1964).

Of course, it is to be understood that such polar organic solubilizing liquids may be employed individually or as mixtures of two or more different polar organic liquid compounds and regardless of whether or not such compounds are employed individually or as mixtures, the amount of such added polar organic solubilizing agents present in the non-aqueous hydroformylation reaction product compositions employable in this invention will in general correspond to that amount employed in the non-aqueous hydroformylation reaction medium of the non-aqueous hydroformylation process from which said non-aqueous hydroformylation reaction product compositions may be derived. For instance, the amount of such added organic solubilizing agent present in any non-aqueous hydroformylation reaction medium of a given non-aqueous hydroformylation process need only be that minimum amount necessary to render the free phosphorus ligand and rhodium-phosphorus ligand complex catalyst that are employed, soluble in the non-aqueous hydroformylation reaction medium at hydroformylation reaction conditions. Accordingly, the amount of such organic solubilizing agent present in the non-aqueous hydroformylation reaction product composition starting materials of this invention correspondingly need only be that minimum amount just defined. In general, it is considered preferable to employ an excess of that minimum required, although no added benefit is seen in employing a huge excess amount. Accordingly when employed, either as individual compounds or as mixtures, the polar organic solubilizing agents may be present in the non-aqueous hydroformylation reaction product composition starting materials of this invention in an amount ranging from about 1 to about 60 weight percent of the non-aqueous hydroformylation reaction product composition (amounts of from about 1 to about 35 weight percent being preferred), since such corresponding amounts of said polar organic solubilizing agents may be employable in the non-aqueous hydroformylation reaction mediums of the hydroformylation processes from which the non-aqueous hydroformylation reaction product compositions of this invention may be derived.

Among the preferred polar organic solubilizing agents are amides, sulfoxides and sulfones, and mixtures thereof, the more preferred polar organic solubilizing agents being amides, for instance, N-methyl pyrrolidone.

More preferably the subject of this invention is one in which the aldehyde product is also highly phase separated from the polar organic solubilizing agent for the rhodium-phosphorus complex and free phosphorus ligand, as well as from said complex and said free ligand. Thus most preferably the subject process of this invention is one in which the amount of added water employed or the sum amount of added water and added non-polar hydrocarbon employed and referred to in the above provisio clause is at least sufficient to provide phase separation of at least about 70 weight percent of the aldehyde contained in the non-aqueous hydroformylation reaction product composition starting material from at least about 95 weight percent of the rhodium-phosphorus complex calculated as rhodium metal, at least 95 weight percent of the free phosphorus ligand and at least 75 weight percent of the polar organic solubilizing agent for said complex and said free ligand also contained in said non-aqueous composition.

Accordingly, the non-aqueous hydroformylation process from which the non-aqueous hydroformylation reaction product compositions employable in this invention may be derived, comprises reacting an olefinically unsaturated organic compound with carbon monoxide and hydrogen in an non-aqueous hydroformylation reaction medium comprising the olefinically unsaturated organic compound, aldehyde product, solubilized rhodium-monosulfonated tertiary phosphine metal salt ligand complex catalyst, solubilized free monosulfonated tertiary metal salt ligand, and an added organic solubilizing agent for said complex catalyst and said free ligand, wherein said organic solubilizing agent is a polar organic liquid solubilizing agent or mixtures thereof, as herein defined above. Further as employed herein said non-aqueous hydroformylation reaction medium, be it in the form of one or more organic phases, is defined as the reaction medium in the hydroformylation reaction zone of the reactor of the non-aqueous hydroformylation process.

Of course it is to be further understood that the non-aqueous hydroformylation reaction product compositions employable in this invention may also contain additional ingredients corresponding to those which have either been deliberately employed in the non-aqueous hydroformylation process from which the non-aqueous hydroformylation reaction product compositions may be derived or which have been formed in situ during the hydroformylation process. For instance, obviously since an olefin starting material is being hydroformylated and is present in the non-aqueous hydroformylation reaction medium, the non-aqueous hydroformylation reaction product composition employed in this invention may and normally will contain at least some unreacted olefin starting material. The amount of such unreacted olefin present in the non-aqueous hydroformylation reaction product composition is in general governed by the efficiency of the hydroformylation process. In general such amounts of unreacted olefin may range from about 2 to about 20 percent of the non-aqueous hydroformylation reaction product composition, although such amounts of unreacted olefin present in the non-aqueous hydroformylation reaction product composition starting materials of this invention are preferably no more than 15 percent by weight and more preferably no more than 10 percent by weight of said non-aqueous hydroformylation reaction product composition. Likewise, minor amounts of in situ type by-products that may be formed during the non-aqueous hydroformylation process may also be correspondingly present in the non-aqueous hydroformylation reaction product composition starting materials of this invention, e.g., in situ type by-products derived from the olefinic starting materials, such as unreacted isomerized olefin, hydrogenated olefin (e.g., corresponding saturated hydrocarbons or paraffin by-products); in situ type by-products derived from the aldehyde products, such as high boiling aldehyde condensation by-products (as described e.g., in U.S. Pat. Nos. 4,148,830 and said 4,731,486 discussed above); and possibly even some in situ type alkyl substituted phosphorus ligand by-product formed by the replacement of one or more of the $R_1$, $R_2$ or $R_3$ radicals of the monosulfonated tertiary phosphine metal salt ligands employed with a saturated alkyl radical corresponding to the olefin starting material employed. Further minor amounts of other additional inert co-solvent type diluents or additives, (such as described e.g., in said U.S. Pat. No. 4,731,486) if employed in the non-aqueous hydroformylation process (although such use is not preferred) may correspondingly be present in the non-aqueous hydroformylation reaction product composition of this invention. Accordingly, it should be sufficient for the purpose of this invention to understand that whatever compounds are present in the hydroformylation reaction medium of the non-aqueous hydroformylation process from which the non-aqueous hydroformylation reaction product composition starting material of this invention is derived, may also be correspondingly present in said non-aqueous hydroformylation reaction product composition starting materials.

As noted above the non-aqueous hydroformylation process serves only as a means for furnishing the non-aqueous hydroformylation reaction product composition employed as the starting material of the phase separation procedure of the present invention and thus the reaction conditions of such hydroformylation processes are not narrowly critical. For instance, in general it is preferred to employ non-aqueous hydroformylation reaction product compositions derived from corresponding non-aqueous hydroformylation reaction processes that employ the operational features taught in U.S. Pat. Nos. 4,731,486 and 4,633,021, especially those of U.S. Pat. No. 4,731,486, the disclosures of said patents being incorporated herein by reference thereto.

Accordingly, the reaction conditions for effecting such non-aqueous hydroformylation processes may be those heretofore conventionally used and may comprise a reaction temperature of from about 45° C. to about 200° C. and pressures ranging from about 1 to 10,000 psia.

While, the total gas pressure of hydrogen, carbon monoxide and olefinic unsaturated starting compound of such non-aqueous hydroformylation processes may range from about 1 to about 10,000 psia, it is preferred that the process be operated at a total gas pressure of hydrogen, carbon monoxide and olefinic unsaturated starting compound of less than about 1500 psia and more preferably less than about 500 psia. The minimum total pressure of the reactants is not particularly critical and depends predominately only on the amount and nature reactants employed to obtain a desired rate of reaction. More specifically the carbon monoxide partial pressure of the non-aqueous hydroformylation process is preferably from about 1 to about 120 psia and more preferably from about 3 to about 90 psia, while the hydrogen partial pressure is preferably about 10 to about 200 psia and more preferably from about 20 to about 160 psia. In general the $H_2$:CO molar ratio of gaseous hydrogen to carbon monoxide may range from about 1:10 to 100:1 or higher, the more preferred hydrogen to carbon monoxide molar ratio being from about 1:1 to about 10:1. Further, it is more preferred to employ a non-aqueous hydroformylation reaction temperature of from about 60° C. to about 130° C. Moreover, while it is clear that the non-aqueous hydroformylation process could be a batch type process, the subject invention is especially useful for improving non-aqueous hydroformylation processes that comprise a continuous liquid rhodium catalyst recycle procedure.

More preferably and specifically the subject invention involves separating the aldehyde product of a non-aqueous hydroformylation reaction product composition corresponding to the non-aqueous hydroformylation reaction medium of a non-aqueous hydroformylation process by treating said composition that has been obtained by withdrawing said medium from the hydroformylation reactor with added water or added water and an added non-polar hydrocarbon compound to induce phase separation or partioning of the components of said composition. For instance, the treated composition rapidly forms two liquid phases or layers upon settling, a non-polar phase consisting essentially of the desired aldehyde products and whatever other non-polar components, e.g. added non-polar compound if employed, that might be present in the treated composition, and a polar phase consisting essentially of the rhodium-phosphorus complex, the free phosphorus ligand, the polar organic solubilizing agent for said complex catalyst and said free ligand, as well as the added water employed in said treatment and whatever other polar components that might be present in the treated composition.

Removal of all or some of the non-aqueous hydroformylation liquid reaction medium from the hydroformylation reactor to obtain the corresponding non-aqueous hydroformylation reaction product composition starting material of this invention can be accomplished in any conventional manner, e.g., in a continuous hydroformylation process a portion of the liquid hydroformylation reaction medium is generally merely continuously pumped from the reactor.

All or part of the corresponding non-aqueous hydroformylation reaction product composition so obtained may then be treated with added water or added water and an added non-polar hydrocarbon compound in accordance with the subject invention and the treated composition phase separated into two distinct liquid layers or phases. Said treatment of the non-aqueous hydroformylation reaction product composition merely involves thoroughly mixing the added water or added water and added non-polar hydrocarbon compound with said composition and said treatment can be carried out in any conventional manner or fashion. Said treatment does not require any special equipment or mixing device, although obviously a thorough mixing of the liquids is desired and harsh mixing which might cause an emulsion is preferably to be avoided. Accordingly, any conventional, suitable mixing equipment and procedure may be employed, e.g., co-current or counter-current mixing, spray columns, static mixing, etc. In general it is preferred to add the water or water and non-polar hydrocarbon compound to the non-aqueous hydroformylation reaction product composition and mix same in one or more spray columns and pass the treated composition on to any conventional type decanter vessel for settling of the two different (i.e., polar and non-polar) liquid phases that are rapidly formed in said vessel. Said mixing treatment and resulting separation, both of which may be accomplished in a matter of minutes, may be carried out at any suitable liquid temperature and pressure. For example, said mixing and phase separation may be carried out at a pressure of from about 1 to about 1500 psia, although lower or higher pressures could be employed if desired. Preferably said mixing and phase separation may be carried out at from about 1 to about 500 psia and more preferably at about atmospheric pressure. It is also preferred to avoid temperatures that are so low that the water employed might freeze (bearing in mind that the organic polar solubilizing agent may lower the freezing point of the water) or that are higher than the hydroformylation reaction temperature used to produce the aldehydes for such might harm the activity or stability of the rhodium complex or otherwise be detrimental to the corresponding non-aqueous hydroformylation process. Accordingly, said mixing and resulting phase separation may be carried out at a liquid temperature of from about $-10°$ C. to $150°$ C., although it is generally preferred to carry out said mixing and phase separation at a liquid temperature of from about $20°$ C. to about $130°$ C. and more preferably from about $20°$ C. to about $110°$ C. Cooling the non-aqueous hydroformylation reaction product composition to a liquid temperature of from about $20°$ C. to $60°$ C. prior to or during said mixing treatment and/or phase separation may aid in obtaining a more complete phase separation of the non-polar and polar ingredients involved.

It is to be further involved understood that while the subject invention is preferably directed to treating a non-aqueous hydroformylation reaction product composition that has been directly obtained by removal of a corresponding liquid reaction medium from the hydroformylation reactor, the non-aqueous hydroformylation reaction product composition starting materials of this invention also encompass any subsequent non-aqueous hydroformylation reaction product composition derived from such an initial composition so obtained, provided of course that said subsequently derived composition is "non-aqueous" as defined herein and contains at least some amount of each of the four main ingredients defined above, i.e., the aldehyde, the rhodium-phosphorus ligand complex, the free phosphorus ligand and the polar organic solubilizing agent for said complex and said free ligand. Moreover, it is to be further understood that the amounts of each of said four main ingredients in such subsequently derived non-aqueous composition starting materials need not necessarily be the same as those amounts of such ingredients present in the non-aqueous hydroformylation reaction product composition from which such subsequent non-aqueous compositions starting materials may be derived. Illustrative possible subsequently derived non-aqueous hydroformylation reaction product compositions may include, e.g., distillation residues obtained upon having removed some of the aldehyde product from an initial non-aqueous hydroformylation reaction product composition obtained from the hydroformylation reactor, or a liquid polar phase obtained by carrying out the subject invention, as well as a liquid polar phase obtained by any other type of phase separation procedure, for instance, certain non-aqueous hydroformylation reaction product compositions obtained directly from the reactor may themselves phase separate into a polar and non-polar phase upon standing merely when cooled to a lower temperature than the hydroformylation reaction temperature, and the like. Thus, if desired, an initial non-aqueous hydroformylation reaction product composition removed from the reactor may be subjected to any suitable pretreatment procedure in order to arrive at a subsequently derived non-aqueous hydroformylation reaction product composition starting material for the subject invention. Moreover, normally the liquid non-polar phase of the subject invention is obtained as the top phase of the phase separation process, while the liquid polar phase is obtained as the bottom phase of said process.

The added non-polar hydrocarbon compound employable to help effect the phase separation of this invention can be any non-polar hydrocarbon compound containing from $C_6$ to $C_{30}$ carbon atoms. Illustrative non-polar hydrocarbons include, e.g., alkanes containing from $C_6$ to $C_{30}$ carbon atoms be they of straight or branched chain structure, such as hexane, heptane, octane, nonane, decane, undecane, dodecane, tridecane, tetradecane, pentadecane, hexadecane, heptadecane, octadecane, nonadecane, eicosane, docosane, tetracosane, hexacosane, octacosane, triacontane and the like; olefinic compounds containing from $C_6$ to $C_{30}$ carbon atoms, such as those corresponding to the olefinic compounds employed in the non-aqueous hydroformylation process from which the non-aqueous hydroformylation reaction product compositions of this invention may be derived, e.g., those olefinic hydroformylation starting materials discussed herein above, especially alpha-olefins containing from $C_6$ to $C_{30}$ carbon atoms; cycloaliphatic compounds containing from $C_6$ to $C_{12}$ carbon atoms, such as cyclohexane, cyclooctane; and the like. Of course, it is to be understood that such non-polar hydrocarbon compounds may be substituted with any substituent that does not adversely effect the phase separation process of this invention. For example, illustrative substituted alkanes include corresponding flurocarbons, and the like. Moreover, mixtures of two or more different non-polar hydrocarbon compounds can be employed if desired, Conveniently the non-polar hydrocarbon compound, when employed, may be one containing the same number of carbon atoms as the olefinic compound that was hydroformylated to produce the desired aldehyde product, although such is not necessary. Preferably, the non-polar hydrocarbon is a saturated straight chain alkane containing from $C_6$ to $C_{30}$ carbon atoms.

The order of addition of the water and non-polar hydrocarbon compound when employed to the non-aqueous hydroformylation reaction product composition is immaterial and they may be added separately and/or simultaneously, or premixed and then added if desired. Moreover, the amount of added water and amount of added non-polar hydrocarbon when employed is not narrowly critical and need only be that minimum amount sufficient to induce the desired phase separation between the non-polar aldehyde product and polar ingredients of the non-aqueous hydroformylation reaction product composition to be treated. Of course, it is to be understood that the terms "added water" and "added non-polar hydrocarbon" as employed herein refer to water and non-polar hydrocarbons that have been deliberately added to the non-aqueous hydroformylation reaction product composition starting materials of this invention for the purpose of the phase separation process of this invention in contrast e.g. to non-polar hydrocarbons that might already be present in said reaction product compositions as an ancillary result of the hydroformylation reaction process itself e.g. unreacted olefin, in situ produced hydrocarbons, hydrocarbons present as the result of employing impure olefin starting materials, and the like, although such amounts of ancillary type non-polar hydrocarbons, if and when present in said hydroformylation reaction product composition starting materials may lessen the amount of deliberately added non-polar hydrocarbon necessary to achieve a particular desired result of phase separation. Indeed it may be possible to deliberately added or provide for some or all of the non-polar hydrocarbon to be present in the hydroformylation reaction medium prior to the removal of said medium from the reactor thereby rendering it necessary to add only water or water and a lesser amount of added non-polar hydrocarbon to the non-aqueous hydroformylation reaction product composition starting material to achieve the desired phase separation benefit that occurs when both added water and added non-polar hydrocarbon are employed. Thus it is to be further understood that while optimization of the amount of added water or sum amount of added water and added non-polar hydrocarbon employed necessary to achieve the best results and efficiency desired in a given situation, will be dependent upon one's experience in the utilization of the subject aldehyde product phase separation invention, such should be easily obtainable by following the teachings of this invention and simple routine experimentation.

Accordingly, the subject process invention comprises mixing the non-aqueous hydroformylation reaction product composition starting material with from about 2 to about 60 percent by weight and more preferably from about 2 to about 30 percent by weight of added water and from 0 to about 60 percent by weight and more preferably from about 2 to 30 percent by weight of an added non-polar hydrocarbon compound, said amounts of added water and added non-polar hydrocarbon compound being based on the total weight of said non-aqueous composition starting material, and by phase separation forming a non-polar phase consisting essentially of aldehyde and the added non-polar hydrocarbon compound when employed, and a liquid polar phase consisting essentially of the added water, the rhodium-phosphorus complex, the free phosphorus ligand and an organic solubilizing agent for said complex and said free ligand; with the proviso that the amount of added water employed or the sum amount of added water and added non-polar hydrocarbon employed is at least sufficient to provide phase separation of at least about 70 weight percent and more preferably at least about 90 weight percent of the aldehyde contained in said non-aqueous composition from at least about 95 weight percent and more preferable at least about 98 weight percent of the rhodium-phosphorus ligand complex calculated as rhodium metal, and recovering said non-polar phase from said polar phase. Preferably said amount of added water employed or the said sum amount of added water and added non-polar hydrocarbon employed is at least sufficient to also provide said phase separation of said aldehyde from at least about 95 weight percent and more preferably at least about 98 of the free phosphorus ligand also contained in said non-aqueous composition, in addition to providing said aldehyde phase separation from said rhodium-phosphorus ligand complex. More preferably said amount of added water employed or the said sum amount of added water and added non-polar hydrocarbon employed is at least sufficient to further also provide said phase separation of said aldehyde from at least 75 and more preferably at least 85 weight percent of the polar organic solubilizing agent for said complex and said free ligand also contained in said non-aqueous composition, in addition to providing said aldehyde phase separation from said rhodium-phosphorus ligand complex and said free phosphorus ligand.

While it has been surprisingly discovered that the above defined proviso results may be accomplished with so little added water alone, the subject invention even more preferably involves accomplishing the above defined proviso results by employing both added water and an added non-polar hydrocarbon compound, instead of merely water alone, the sum amount of both said additions being in the range of from about 5 to about 60 percent by weight, preferably about 10 to about 50 percent by weight, based on the total weight of the non-aqueous hydroformylation reaction product composition to be treated. Indeed it has been surprisingly discovered that the employment of both added water and an added non-polar hydrocarbon appears to result in a beneficial synergistic effect with regard to better achieving the optimum overall desired phase separation results discussed above with regard to all four of the main components in the starting composition, as compared to that achievable when adding comparative amounts of only water alone or only a non-polar hydrocarbon compound alone.

Moreover the desired phase separation results of this subject invention may be achieved by a single phase separation step in contrast to any need for two or more repeated phase separation procedures. In general, it is preferred to treat the non-aqueous hydroformylation reaction product composition by mixing it with added water or added water and an added non-polar hydrocarbon compound in any suitable manner and allowing the treated composition to settle into the non-polar and polar phase in any suitable liquid decanter. Alternatively, if desired, the subject phase separation invention may be carried out directly in any conventional cocurrent or counter-current liquid-liquid extractor.

While the aldehyde containing liquid crude non-polar phase obtained by the subject invention need not necessarily be further purified from non-polar hydrocarbon compounds and/or possible polar compounds that might also be present in said non-polar phase prior to using said aldehyde, e.g., as a starting material for producing alcohols via hydrogenation, such purification if desired and can be accomplished by any conventional means. For example, polar compounds may be removed from aldehyde containing liquid crude non-polar phase so obtained by employing any conventional cocurrent or counter-current liquid-liquid extractor, while separation of the aldehyde products from other non-polar compounds may be accomplished by simple distillation. Hydrocarbon compounds separated from the aldehyde product, either before and/or those recovered after hydrogenation of the aldehyde product may be recycled or used if desired as the non-polar hydrocarbon additive in the treatment of the non-aqueous hydrocarbon reaction product composition of this invention. Moreover, it is preferred that the aldehyde containing liquid crude non-polar phase obtained by the subject invention, especially for economic reasons, at least be purified from the possible amounts of polar compounds that may be present therein, such as the rhodium-phosphorus ligand complex, free phosphorus ligand, and the polar organic solubilizing agent for said complex and said free ligand, by employing a counter-current liquid-liquid extractor. For instance, water can be used in a counter-current liquid-liquid extractor to remove the polar compounds from the aldehyde containing liquid crude non-polar phase obtained by this invention. Moreover, if desired a small amount of the monosulfonated tertiary phosphine metal salt ligand present in the non-aqueous hydroformylation reaction product composition starting materials of this invention, or any other suitable rhodium scavenger, may be added along with the water to the extractor to help scavenge any rhodium that might be present. Because of the high expense of rhodium it is naturally desirable to recover as much of such rhodium as economically feasible. The aqueous containing polar composition obtained from the extractor may be recycled into the system as desired. For instance, if desired, all or a portion of the aqueous polar solution recovered from the extractor may be employed as the source of water added to the non-aqueous hydroformylation reaction product composition starting material of this invention by recycling it to the non-aqueous hydroformylation reaction product composition to be treated in accordance with this invention.

The aqueous rhodium-phosphorus complex containing liquid polar phase that has been phase separated from the aldehyde by the process of the subject invention, after removal of the water, is preferably recycled back to the hydroformylation reactor of the non-aqueous hydroformylation reaction process from whence the non-aqueous hydroformylation reaction product composition starting materials have been derived, in order to achieve a continuous, liquid catalyst recycle, non-aqueous hydroformylation process. The water may be removed from the aqueous rhodium-phosphorus complex containing polar phase by any conventional method, such as by pumping it to any conventional vaporizer-separator. The non-aqueous rhodium-phosphorus complex containing polar composition (which also contains free phosphorus ligand and polar organic solubilizing agent for said complex and said free ligand) accumulated from the vaporizer-separator may then be recycled back to the hydroformylation reactor. Of course if desired two or more vaporizer-separators can be employed so that the aqueous separation process is repeated, e.g., the aqueous liquid removed from the first vaporizer being employed as the feed for the second vaporizer-separator and the vaporizer overhead accumulated from the second vaporizer recycled to the first vaporizer-separator. In addition, all or a portion, as desired, of the aqueous polar solution obtained from the liquid-liquid extractor discussed above may also have its water removed by conveying said aqueous polar composition to a vaporizer-separator as mentioned above and its resultant non-aqueous polar solution also returned to the hydroformylation reactor if desired. For efficiency purposes and in order to avoid undue aqueous wetting of the rhodium-phosphorus ligand complex in the main liquid polar aqueous phase composition obtained, e.g., from a simple decanter, it may be preferred to employ a different vaporizer-separator, if water is to be removed from any additional liquid polar solutions that might be obtained (e.g., from the liquid-liquid extractor used to purify the main liquid aldehyde containing non-polar phase obtained by the process of the subject invention) rather than the same vaporizer-separator employed to remove water from said main liquid polar aqueous phase.

Removal of the water from an aqueous rhodium-phosphorus ligand complex containing polar phase by means of a vaporizer-separator as discussed above, may and normally will also cause some vaporization removal of the polar organic solubilizing agent also present in the aqueous polar phase. Thus, while the water and other vaporized materials obtained from a vaporizer-separator may be condensed and reused if desired, e.g., as part of the water added to the liquid-liquid extractor column as discussed above, economic reasons may dictate the desirability of first separating and recovering the vaporized polar organic solubilizing agent from the water and reusing the condensed polar non-aqueous organic solubilizing agent composition so obtained by recycling it back to the hydroformylation reactor. Likewise, it may be desirable to also separate and recover organic polar solubilizing agent from the water of the aqueous solution obtained from a liquid-liquid extractor as discussed above. Such separation of the water and organic polar solubilizing agent may be accomplished by any conventional method, such as by employing a conventional distillation column wherein said materials are refluxed to separate and obtain both water and the organic polar solubilizing agent composition from the distillation column. The separated non-aqueous organic polar solubilizing agent stream so recovered may then be recycled to the hydroformylation reactor in any manner desired, while the separated water so obtained may be recycled and reused in any manner desired, e.g., as part or all of the water added to the liquid-liquid extractor.

Accordingly, the subject invention involving the separation of the aldehyde product from a non-aqueous hydroformylation reaction product composition not only provides a unique technical advancement in the art with regard to such above discussed overall separation of all four main ingredients or components in general, but also provides for a uniquely self-contained separation system, wherein, e.g., the small amount of added water employed need only be added to the system a single time, since the same water employed to effect said separation may be continuously recycled and reused, in a closed system. There is no need for additional charges of supplemental new water to such a closed system although additional amounts of supplemental new water could be employed if desired. Further an additional benefit of this invention is the resultant improved overall continuous liquid catalyst recycle, non-aqueous hydroformylation process that is also provided for by the subject invention and its attendant benefits as disclosed herein.

Accordingly another aspect of this invention may be described as an improved continuous liquid catalyst recycle, non-aqueous hydroformylation process for producing aldehydes which comprises hydroformylating an olefinic compound with carbon monoxide and hydrogen in the presence of a solubilized rhodium-monosulfonated tertiary phosphine metal salt ligand complex catalyst, solubilized free monosulfonated tertiary phosphine metal salt ligand and a polar organic solubilizing agent for said complex catalyst and said free ligand, in a hydroformylation reactor, obtaining therefrom a non-aqueous hydroformylation reaction product composition comprising the aldehyde product, the rhodium-monosulfonated tertiary phosphine metal salt ligand complex, the free monosulfonated tertiary phosphine metal salt ligand and the polar organic solubilizing agent for said complex and said free ligand, separating and recovering aldehyde product from said non-aqueous composition, and recycling the remaining rhodium-monosulfonated tertiary phosphine metal salt ligand complex containing liquid which also contains said free monosulfonated tertiary phosphine metal salt ligand and said polar organic solubilizing agent to the hydroformylation reactor after said separator of aldehyde product, the improvement comprising separating said aldehyde product from said non-aqueous hydroformylation reaction product composition by mixing said non-aqueous composition with from about 2 to about 60 percent by weight by added water and from 0 to about 60 percent by weight of an added non-polar hydrocarbon compound, said amounts of added water and added non-polar hydrocarbon compound being based on the total weight of said non-aqueous composition, and by phase separation forming a liquid non-polar phase consisting essentially of aldehyde and the added non-polar hydrocarbon when employed, and a liquid polar phase consisting essentially of the added water, the rhodium-monosulfonated tertiary phosphine metal salt ligand complex, the free monosulfonated tertiary phosphine metal salt ligand and the polar organic solubilizing agent for said complex and said free ligand, recovering said non-polar phase from said polar phase, and recycling said polar phase after removal of the water to the hydroformylation reactor, with the proviso that said amount of said water employed or said sum amount of added water and added non-polar hydrocarbon employed is at least sufficient to provide phase separation of at least about 70 weight percent and more preferably at least about 90 weight percent of the aldehyde contained in said non-aqueous composition from at least about 95 weight percent and more preferable at least about 98 weight percent of the rhodium-monosulfonated tertiary phosphine metal salt ligand complex calculated as rhodium metal also contained in said non-aqueous composition. Of course it is to be understood that the generic and preferred ingredients or components and processing conditions of said improved continuous liquid catalyst recycle, non-aqueous hydroformylation process may correspond to those ingredients or components and processing conditions disclosed and discussed elsewhere in this subject specification.

Thus as described above, the subject invention may be further depicted by referring to the Figure of the drawing, wherein syn gas (CO and $H_2$) and the olefinic compound to be hydroformylated may be fed e.g., through lines 1 and 2 into a hydroformylation zone e.g., oxo reactor 101, which contains the rhodium-phosphorus ligand complex catalyst, free phosphorus ligand and the polar organic solubilizing agent for said complex catalyst and said free ligand, and wherein the non-aqueous hydroformylation of the olefinic compound to aldehyde product takes place. All or a portion of the corresponding liquid aldehyde containing non-aqueous hydroformylation reaction product medium may be continuously withdrawn from the hydroformylation reactor 101 to provide the non-aqueous hydroformylation reaction product composition starting material of this invention e.g., via line 4. Water and/or water and a non-polar hydrocarbon may then be added to said withdrawn reaction product composition, e.g., via lines 3 and 12, and thoroughly mixed therewith, in a mixer e.g., 102, such as a series of cocurrent spray columns having alternating heavy and light continuous phases, and the resultant treated hydroformylation reaction product composition conveyed e.g., via line 4a to a liquid decanter vessel, e.g., 103, wherein said treated composition rapidly settles into two distinct liquid phases, i.e., a non-polar phase consisting essentially of the desired aldehyde product and e.g., unreacted olefin and non-polar hydrocarbon additive of line 3 when employed, and a liquid polar phase consisting essentially of the rhodium-phosphorus ligand complex, free phosphorus ligand, the polar organic solubilizing agent for said complex and said free ligand, and the water additive of line 12. The liquid aldehyde containing non-polar phase may be removed from the decanter vessel 103, e.g., via line 5 and conveyed to a liquid-liquid extractor e.g., 104. Polar compounds that might also be present in said liquid aldehyde containing phase may be removed therefrom with the aid of water (and a rhodium scavenger if desired, e.g., a corresponding monosulfonated tertiary phosphine metal salt ligand via, e.g. line 15) added to said liquid-liquid extractor 104 via, e.g., line 13 and the desired purified liquid aldehyde product may be obtained and recovered from said extractor, e.g., via line 9. Said aldehyde product so obtained which may still contain some additional non-polar hydrocarbon compounds such as the unreacted olefin and the non-polar hydrocarbon additive when employed may be further purified if desired in any conventional manner not shown, e.g., by distillation. The aqueous rhodium-phosphorus ligand complex containing liquid polar phase in said decanter 103 may be removed therefrom, e.g., via line 6 and conveyed to a vaporizer-separator e.g., 105 for removal of the water, and the non-aqueous rhodium-phosphorus ligand complex containing composition obtained therefrom recycled to the hydroformylation reactor, e.g., via line 8. Moreover, all or a portion of the aqueous composition obtained from said liquid-liquid extractor 104 e.g., via line 10 may be conveyed e.g. via line 12 to the non-aqueous hydroformylation reaction product composition to be treated or all or a portion of said aqueous composition may be conveyed e.g. via line 11 to a distillation column e.g., 106, wherein the water may be separated from any of the other polar compounds that may be present such as the polar organic solubilizing agent. In general it is preferred to divide the aqueous composition of said line 10 into two streams, one stream serving as the source of said line 12 and the other as the source of said line 11. The purified water from said distillation column 106 may be reused and returned to said liquid-liquid extractor 104 e.g., via line 13, while the polar compounds such as the polar organic solubilizing agent obtained from said distillation column 106 may be recycled to the hydroformylation reactor 101 e.g., via line 14.

Additional and other embodiments of the Figure drawing may be found further disclosed herein and/or will be obvious to one skilled in the art. For instance, the source of water added to the non-aqueous hydroformylation reaction product composition via line 12 to be treated need not be derived from the aqueous composition of line 10 but could be from a different supply of water e.g. from line 13 or some other source not shown. The same is also true of water added to extractor 104 via line 13, it also could be from a supply of water not shown. For example, obviously an initial supply of water is needed at the start up of the process and such may be accomplished by adding said water to line 12 or line 13 or in any other appropriate manner not shown. Moreover, if desired all or part of the aqueous composition of line 10 could first go to vaporizer-separator not shown, the water and vaporized materials collected therefrom going to distillation column 106 and the vaporizer tails going to vaporizer-separator 105 or some other vaporizer-separator, not shown.

It is to be further understood that mixer 102 and decanter 103 could be omitted if desired and the non-aqueous hydroformylation reaction product composition of line 4 along with the added hydrocarbon of line 3 if employed conveyed directly to the liquid-liquid extractor 104, water being added to said extractor in a cocurrent or more preferably a counter-current manner e.g., via line 13.

The following examples are illustrative of the present invention and are not to be regarded as limitative. It is to be understood that all parts, percentages and proportions referred to herein and in the appended claims are by weight unless otherwise indicated.

It has now been surprisingly discovered that phosphinoalkylsulfonate salt ligands, (i.e. ligands having the above depicted general formula (I) wherein $R_3$ represents a divalent alkylene radical are far more resistant to ionic group interchanging or scrambling under hydroformylation reaction conditions than phosphinoarylsulfonate salt ligands, i.e. ligands of the above depicted general formula (I) wherein $R_3$ represents a divalent 1,3-phenylene radical. For instance, it appears that tertiary organo groups of an ionic phosphine ligand salt containing a sulfonated aryl group are readily susceptible to group interchanging or scrambling under hydroformylation reaction conditions, while such does not appear to be the case for such ligands that contain a sulfonated alkyl group instead of said sulfonated aryl group.

More specifically, e.g., it has been found that the monosulfonated triphenylphosphine sodium salt (i.e. TPPMS-Na) exhibits extensive aryl group scrambling under hydroformylation reaction conditions to form such equilibrated counterparts as di- and trisulfonated triphenylphosphine sodium salts as well as unsulfonated triphenylphosphine as shown by the following equilibration:

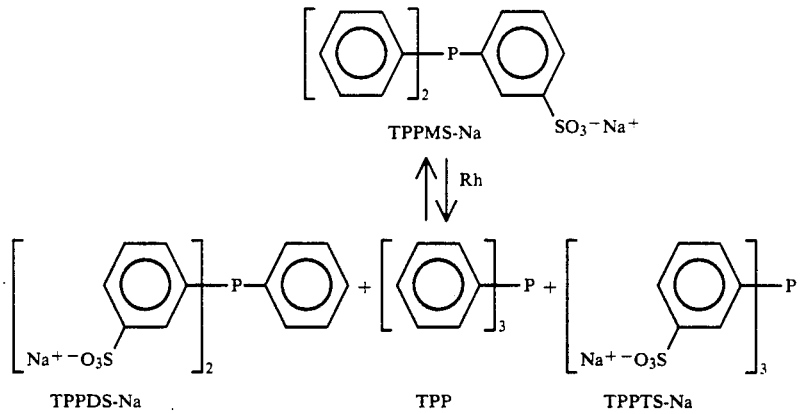

Such ligand decomposition can obviously have a substantial and adverse effect towards obtaining the desired prolonged, stable continuous hydroformylation process of this invention. For instance, a consequence of the formation of such aryl scrambling products is that multiple sulfonated charged ligands are formed causing a change in the catalyst solubility and polarity characteristics which can adversely affect the reactivity of the monosulfonated phosphine ligand containing rhodium complex catalysts employable in this invention. The di- and trisulfonated scrambling product phosphine ligands are not readily soluble in organic media such as N-methyl pyrrolidone and in addition provide inherently lower catalyst reactivity (than the mono-sulfonated phosphine ligands employable in this invention) thus eventually giving rise to a net catalyst deactivation, as well as ligand and/or complex catalyst phase separation, in the hydroformylation process of this invention.

In addition to such drawbacks caused by the formation of such di- and trisulfonated phosphine ligands, another and possibly even more important problem of such ligand decomposition or scrambling is the formation of the non-ionic unsulfonated triphenylphosphine ligand which is "oil"-soluble, i.e. soluble in the aldehyde product. For instance, since a major aspect of the subject processes of this invention involves the phase separation of the aldehyde product from the rhodium-ligand complex catalyst and free ligand employed in the hydroformylation process, obviously such scrambled non-ionic unsulfonated triphenylphosphine ligand which is soluble in such aldehydes will be readily removed and lost from the hydroformylation process along with the separation and recovery of the aldehyde product. Further as seen by the above scrambling equilibration reactions, any permanent loss of such non-ionic unsulfonated triphenylphosphine will shift the equilibration towards the formation of more di and trisulfonated scrambled phosphine ligands.

In contrast diphenylphosphinoalkylsulfonate salt ligands such as 3-(diphenylphosphino) propylsulfonate—sodium salt (DPPS-NA) having the formula

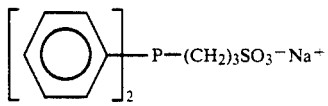

and 4-(diphenylphosphino) butylsuflonate—sodium salt (DPBS-Na) having the formula

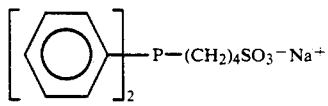

have been found to be virtually completely stable against exhibiting any aryl/alkyl group scrambling under the same hydroformylation type conditions that promoted the extensive scrambling of the above mentioned TPPMS-NA ligand. Thus phosphino-alkylsulfonate salt ligands of the general formula

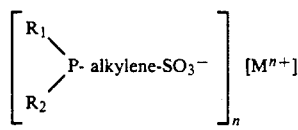

wherein the divalent alkylene radical, $R_1$, $R_2$, M and n are the same as defined herein above, are now considered to be the more preferred ligands of choice for use as the free phosphorus ligand and ligand of the rhodium-phosphorus complex catalyst in the processes of this invention. The use of such phosphinoalkylsulfonate salt ligands in general provides for much higher chemical ligand and catalyst stability thus improving both the lifespan of the active catalyst and the processes of this subject invention. Moreover, while the processing conditions of the processes of this invention previously described herein above remain applicable, the use of such phosphinoalkyl sulfonate salt ligands also readily allow for good overall results when the amount of added water employed or the sum amount of added water and added non-polar hydrocarbon employed in the processes of this invention is at least sufficient to provide phase separation of at least about 90 weight percent of the rhodium-phosphorus ligand complex calculated as rhodium metal, and more preferably to also provide phase separation of at least about 90 weight percent of the free phosphorus ligand, contained in the non-aqueous composition, in addition to providing the phase separation of at least about 70 weight percent of the aldehyde also contained in the non-aqueous composition from said rhodium-phosphorus liagnd complex and said free phosphorus ligand.

While illustrative examples of such phosphinoalkylsulfonate salt ligands include those that have been shown herein above; the more preferred ligands are those of the general formula

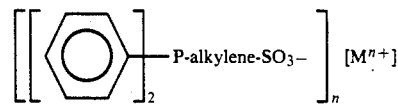

wherein the divalent aklylene radical contains from 2 to5 carbon atoms and wherein n and M are the same as defined above. More preferably M represents an alkali metal such as sodium. Again illustrative diphenylphosphinoalkyl sulfonated salt ligands include e.g.
DPES-Na; i.e. $Ph_2PCH_2SO_3^-Na^+$
DPPS-Na; i.e. $Ph_2P(CH_2)_3SO_3^-Na^+$
DPPS-Li; i.e. $Ph_2P(CH_2)_3SO_3^-Li^+$
DPBS-Na; i.e. $PH_2P(CH_2)_4SO_3^-Na^+$
$[DPBS]_2$-Ca; i.e. $[Ph_2P(CH_2)_4SO_3^-]_2$ $Ca^{++}$
wherein each Ph represents a phenyl radical; and the like, the most preferred ligands being DPPS-Na and DPBS-Na, especially DPBS-Na.

Phase separation of the aldehyde product from compositions also containing the rhodium-phosphorus ligand complex, free phosphorus ligand and an organic solubilizing agent for said complex and said free ligand, wherein the ligand of said complex and said free ligand is a phosphinoalkylsulfonate salt, as described herein by the processes of this invention which employ water or water and a non-polar hydrocarbon compound, result in phase separated non-polar aldehyde product solutions that may be cloudy in appearance as opposed to non-cloudy phase separated non-polar aldehyde product solutions obtainable when phosphinoaryl-sulfonate salt ligands as described herein are employed. Such cloudy phase separated aldehyde product solutions are considered to be due to the entrainment of droplets of a finely dispersed emulsion and/or micelles of the polar phase (i.e. added water as well as the rhodium-phosphorus ligand complex, free phosphorus ligand, organic solubilizing agent for said complex and said free ligand) throughout the obtained non-polar aldehyde product phase. A number of variables, such as the type of ligand and/or organo solubilizing agent employed may have an effect on the dispersal of the polar phase droplets or micelles in said non-polar phase. Another factor to consider is the speed at which said non-polar and polar phases will separate from each other upon settling. For example the use of diphenylphosphino propyl and butyl sulfonate sodium salt ligands (DPPS-Na and DPBS-Na) in the processes of this invention have been found to result in aldehyde product-catalyst phase separation that proceeds at a rapid rate for the first hour and then at a much slower rate after that. However such a dispersal of a small portion of the polar phase in the desired separated non-polar aldehyde containing phase is more than off-set by the excellent ligand and catalyst stability as well as the very good rate of hydroformylation and high normal to isomer aldehyde product ratio that can be provided by the use of the now preferred phosphinoalkylsulfonate salt ligands described herein above.

Further it has been surprisingly discovered that such a dispersed polar phase (involving the rhodium-ligand complex, free ligand, polar organic solubilizing agent and added water), which is not readily removable from the polar aldehyde product phase by liquid-liquid extraction, can now be easily and virtually totally removed and recovered by thoroughly contacting the obtained crude non-polar aldehyde product phase containing the dispersed polar phase droplets or micelles with any suitable inorganic or carbonaceous adsorbent for said dispersed polar phase. For instance, said crude non-polar aldehyde product phase contaminated with said dispersed polar phase may be passed through any such suitable inorganic or carbonaceous adsorbent bed to remove some or virtually all of the dispersed polar phase that might be present in the obtained non-polar aldehyde product phase (e.g. line 9 of the liquid-liquid extractor (104) of the depicted Figure of the drawing described herein). Of course if desired more than one such adsorbent bed, e.g. a series of such beds, may be employed and any such bed may be easily removed and/or replaced, and/or regenerated as required or desired.

Any suitable adsorbent may be employed herein. Illustrative adsorbents include inorganic adsorbents, such as silica gel, activated alumina, diatomaceous earth, kieselguhr, silica-alumina gel, vermiculite, molecular sieves, mordemite, and the like; and carbonaceous adsorbents such as activated carbon, carbon molecular sieves, and the like. See also "Principles of Adsorption and Adsorption Processes" by D. M. Ruthven, 1984, pp 4-19. (John Wiley & Sons, Inc., publishers, New York) for further adsorbent information. Preferably, the adsorbent is inorganic, silica gel being the most preferred. Such types of adsorbent compounds and beds and/or methods for their manufacture are well known.

The use of an adsorbent bed to effectively render the desired aldehyde product of the processes of this invention virtually free of any such dispersed polar phase components may be readily monitored e.g. by measuring the amount of rhodium and free ligand in the aldehyde liquid prior to being passed through the adsorbent bed as compared to the amount of rhodium and free ligand in the aldehyde liquid after it has been passed through the adsorbent bed. In addition, visual evidence may be seen by the fact that the cloudy aldehyde starting liquid entering into the adsorbent bed may emerge from such a bed as a crystal clear liquid, while evidence of polar phase component retention on said bed is witnessed by a yellow band that appears on the otherwise white silica gel adsorbent bed. Experience has shown that even minor and trace amounts of rhodium and ligand may be removed to below detectable amounts from a crude aldehyde product that contains some dispersed polar phase droplets or micelles as discussed above.

In addition it has been further surprisingly discovered that such used and/or exhausted adsorbent beds may be easily and readily virtually completely regenerated merely by backflushing the contained polar phase components from the used adsorbent bed, with any suitable polar solvent. Any polar organic solvent for the rhodium-ligand complex catalyst and free ligand may be employed, illustrative examples of such solvents including those polar organic solvents herein discussed above, a preferred solvent being N-methyl pyrrolidone. Of course, the amount of solvent employed obviously need only be that amount necessary to remove the desired amount the polar phase contained by the adsorbent bed in question and such backflushing can be carried out at ambient temperature and in as many stages as desired. However, it is further preferred to also wash any excess polar solvent from said treated adsorbent bed by further backflushing the polar solvent treated bed with a non-polar compound such as a high molecular weight hydrocarbon or aldehyde. Preferred non-polar compounds include the olefin strating materials and aldehyde products of this invention, as well as their corresponding alkane counterparts, such as described herein above.

The success of any said regeneration of the silica gel adsorbent bed may be visually witnessed by the removal of the yellow band from the used adsorbent bed and the restoration of the adsorbent bed to its original white appearance. The liquid recovered by said backflushing procedures may be returned to the hydroformylation process in any fashion desired for reuse of the recovered rhodium and ligand.

Further, in view of the fact that the adsorbent bed treatment encompassed herein is designed to remove and recover any part and more preferably virtually all of the dispersed polar phase contained in the obtained crude non-polar aldehyde product phase as discussed above, it is apparent that specific values cannot be arbitrarily given to such conditions as the design, number and positioning of the adsorbent bed in the reaction system, temperature and contact time for the treatment. Such conditions are not narrowly critical and obviously need only be at least sufficient to obtain the improvement desired. For instance, the subject invention contemplates the employment of and adsorbent bed through which the obtained crude aldehyde product liquid, such as stream #9 emerging from the liquid-liquid extractor #104 of the figure drawing of this invention, may be passed. Moreover, the number of beds employed, as well as their positioning in the reaction system involved is also not considered absolutely critical and need only be such that it is suitable to obtain the result desired. Likewise, treatment conditions such as temperature, pressure and contact time may also vary greatly, depending on the wishes of the operator and any suitable combination of such conditions may be employed herein so long as the desired effectiveness of the treatment is achieved. Likewise, the temperature is preferably carried out at ambient temperature and under normal operating pressures within the system employed although higher or lower pressure may be employed if desired, while the contact time of the liquid passing through the adsorbent bed may also need only be sufficient to achieve the desired results.

Accordingly, an even more preferred aspect of this invention involves a continuous liquid catalyst recycle, non-aqueous hydroformylation process for producing aldehydes as described herein, the improvement comprising employing as the free phosphine ligand and ligand of the rhodium complex catalyst a phosphinoalkyl sulfonate salt such as DPBS-Na. Moreover, the crude non-polar aldehyde product obtained from said process that contains droplets of a finely dispersed emulsion and/or micelles of the polar phase throughout said crude non-polar aldehyde product, can be passed through a suitable adsorbent bed e.g. silica gel so as to remove the polar phase from said aldehyde product.

According another aspect of this invention may be described as a novel process for removing dispersed droplets of a finely divided emulsion and/or micelles of a polar phase as described herein above, (e.g., a polar phase consisting essentially of water, a rhodium-phosphorus ligand complex, free phosphorus ligand and an organic solubilizing agent for said complex and said free ligand, wherein the ligand of said complex and said free ligand is a phosphinoalkylsulfonate salt ligand as described herein) contained in a non-polar aldehyde containing phase by passing said contaminated non-polar aldehyde containing phase through a carbonaceous or inorganic adsorbent bed so as to remove said polar phase from said non-polar aldehyde phase. This novel process, as well as the preferred components and processing conditions, have already been herein discussed above.

Various modifications and variations of this invention will be obvious to a worker skilled in the art and it is to be understood that such modifications and variations are to be included within the purview of this application and the spirit and scope of the appended claims.

EXAMPLE 1

This comparative example illustrates the phase separation of the aldehyde product (as well as the partioning of other components) from a simulated non-aqueous hydroformylation reaction product composition containing nonanal aldehyde, unreacted octene-1, a rhodium phosphine ligand complex, free phosphine ligand and a polar organic solubilizing agent for said complex and said free ligand, by merely cooling the composition to room temperature (about 25° C.) in the absence of water.

A liquid mixture containing about 0.0378 grams of rhodium dicarbonyl acetylacetonate complex (about 500 ppm rhodium), about 4.8 grams of a monosulfonated triphenylphosphine sodium salt ligand (TPPMS-Na) having the formula

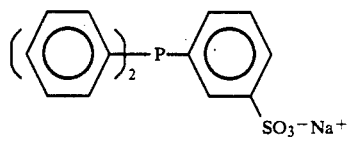

(the mole ratio of said ligand to rhodium being about 90 to 1), about 9.0 grams of N-methylpyrrolidone (as the polar organic solubilizing agent), and about 16.2 grams of a 6:3:1 (wt.:wt.:wt. percent ratio) mixture of unrefined nonanal aldehyde (containing an estimated amount of about 10% of mixed octenes), nonanal dimer and octene-1, was prepared and heated to 100° C. and then allowed to cool to about 25° C. Said liquid mixture was a homogeneous (one phase) composition at 100° C. which phase separated into two liquid phase layers upon cooling to about 25° C. Analysis of each liquid layer by gas chromatography (GC) for the volatile nonanal aldehyde, nonanal dimer, octene-1 and N-methylpyrrolidone (NMP) components; by high performance liquid chromatography (HPLC) for the free phosphine ligand (TPPMS-Na) and by atomic adsorption spectroscopy (AAS) for rhodium metal (Rh) was conducted and the results are given in Table 1 below.

TABLE 1

| Component | Weight Percentage of Each Component in Each Liquid Layer | |
|---|---|---|
| | Non-Polar Phase | Polar Phase |
| Nonanal Aldehyde | 90 | 10 |
| Nonanal Dimer | 96 | 4 |
| Octene-1 | 97 | 3 |
| N-Methylpyrrolidone | 63 | 37 |
| Rhodium | 8 | 92 |
| TPPMS-Na Ligand | 6 | 94 |

The above results demonstrate that while phase separation occurred upon merely cooling the homogeneous composition, a significant amount of the rhodium, phosphine ligand and polar organic solubilizing agent was contained in the non-polar phase along with the aldehyde.

EXAMPLE 2

This example illustrates the improvement in phase separation of the aldehyde product over that obtained in Example 1 as a result of the addition of water.

About 10 percent by weight of water was added to a liquid mixture that had the same composition and was prepared in the same manner as described in Example 1 and the aqueous mixture allowed to phase separate into two liquid layers at 25° C. temperature. Analysis of each liquid layer by the same GC, HPLC and AAS methods described in Example 1 was conducted and the results are given in Table 2 below.

TABLE 2

| Component | Weight Percentage of Each Component in Each Liquid Layer | |
|---|---|---|
| | Non-Polar Phase | Polar Phase |
| Nonanal Aldehyde | 100 | 0 |
| Nonanal Dimer | 100 | 0 |
| Octene-1 | 100 | 0 |
| N-Methylpyrrolidone | 18 | 82 |
| Rhodium | 1 | 99 |
| TPPMS-Na Ligand | 0.1 | 99.9 |

The above results show a substantial improvement in aldehyde separation from the rhodium, phosphine ligand and polar organic solubilizing agent in the liquid mixture over that shown in Table 1 of Example 1.

EXAMPLE 3

This example illustrates the effect of adding varying amounts of water to a simulated non-aqueous hydroformylation reaction product composition containing tridecanal aldehyde, unreacted dodecene, a rhodium-phosphine ligand complex, free phosphine ligand and a polar organic solubilizing agent for said complex and, free ligand, in order to minimize the loss of rhodium due to its phase separation along with the aldehyde in the non-polar phase.

A liquid mixture containing about 0.0225 grams of rhodium dicarbonyl acetylacetonate complex, (about 300 ppm rhodium), about 4.8 grams of TPPMS-Na, i.e., the same phosphine ligand shown employed in Example 1 (the mole ratio of said ligand to rhodium being about 150 to 1), about 15 grams of N-methylpyrrolidone (as the polar organic solubilizing agent), and about 10.2 grams of a 10:1 (wt.:wt. percent ratio) mixture of unrefined tridecanal aldehyde (containing an estimated amount of about 10% mixed dodecenes) and dodecene-1 was prepared and became a homogeneous (one phase) composition upon heating to 90° C. This homogeneous composition was separated into three equal sample portions. One sample was allowed to cool to about 25° C. where it phase separated into two liquid layers. To the second and third samples were added 0.5 and 1.0 grams of water respectively at 90° C. and the two samples allowed to cool to about 25° C. and phase separate into two liquid layers. The addition of said water to the second and third samples caused phase separation even at 90° C. The phase separated non-polar top layers (which consist essentially of the tridecanal and dodecene-1 liquids) of each sample at 25° C. were analyzed for rhodium by atomic absorption spectroscopy and the results are given in Table 3 below.

TABLE 3

| Sample | Water (wt. %) Added | Rhodium (ppm) in Non-Polar Top Phase |
| --- | --- | --- |
| 1 | 0 | 86.4 |
| 2 | 5 | 2.9 |
| 3 | 10 | 1.1 |

The above results show that the addition of a small amount of water can substantially minimize the amount of rhodium that may be phase separated into the non-polar phase along with the aldehyde.

EXAMPLE 4

This example illustrates the effect of adding various amounts of water to simulated non-aqueous hydroformylation reaction product compositions containing different high molecular weight aldehydes and their olefin precursors, a rhodium-phosphine ligand complex, free phosphine ligand and a polar organic solubilizing agent for said complex and said free ligand, in order to minimize rhodium loss due to its phase separation along with the aldehyde in the non-polar phase.

Various liquid mixtures were prepared each containing about 300 ppm rhodium as rhodium dicarbonyl acetylacetonate complex, about 16 wt. % of TPPMS-Na, i.e., the same phosphine ligand shown employed in Example 1, (the mole ratio of ligand to rhodium being about 150 to 1 in each instance), N-methylpyrrolidone (NMP) as shown in Table 4 below and the balance in each instance being a 2:1 wt. to wt. percent mixture of various unrefined aldehydes (each containing an estimated amount of from about 8 to about 12% of corresponding mixed olefins) and their corresponding alpha-olefin precursors as also shown in Table 4 below. Each liquid mixture formed a homogeneous (one phase) composition upon being heated to 90° C. To each liquid mixture various amounts of water were added at 90° C. and each aqueous mixture was allowed to cool to about 25° C. and phase separate into two liquid layers. The phase separated non-polar top layers (which consist essentially of the aldehyde and olefin) of each mixture were each analyzed at 25° C. for rhodium by atomic absorption spectroscopy and the results are given in Table 4 below.

TABLE 4

| Aldehyde/Olefin-1 Mixture | NMP (Wt. %) | Water added (Wt. %) | Rhodium (ppm) in Non-Polar Top Phase |
| --- | --- | --- | --- |
| Heptanal/Hexene-1 | 20 | 10 | 1.8 |
| Heptanal/Hexene-1 | 20 | 20 | <1.0 |
| Nonanal/Octene-1 | 30 | 5 | 2.1 |
| Nonanal/Octene-1 | 30 | 10 | 1.3 |
| Undecanal/Decene-1 | 45 | $10^b$ | 1.0 |
| Tridecanal/Dodecene-1 | 50 | $5^b$ | 2.9 |
| Tridecanal/Dodecene-1 | 50 | $10^b$ | 1.1 |
| Pentadecanal/Tetradecene-1 | 60 | $5^b$ | 2.9 |
| Pentadecanal/Tetradecene-1 | 60 | $10^b$ | 0.8 |

$^b$Exhibited phase separation at ambient temperature (about 25° C.) even before addition of water The above results illustrate that the addition of a small amount of water greatly minimized the amount of rhodium that may be phase separated into the non-polar phase along with the variety of different aldehydes used.

EXAMPLE 5

This example illustrates the effect of adding various amounts of water, or a non-polar hydrocarbon, or both water and a non-polar hydrocarbon to a simulated non-aqueous hydroformylation reaction product composition in order to enhance phase separation of the aldehyde from the composition while minimizing the loss of rhodium, free ligand and polar organic solubilizing agent due to their phase separation along with the aldehyde in the non-polar phase.

A liquid mixture containing about 300 ppm rhodium as rhodium dicarbonyl acetylacetonate complex, about 10 weight percent of TPPMS-Na, i.e., the same phosphine ligand shown employed in Example 1 (the mole ratio of said ligand to rhodium being about 95 to 1), about 50 weight percent of NMP, i.e., N-methylpyrrolidone (as the polar organic solubilizing agent), and about 40 weight percent of a 10:1 (wt:wt % ratio) mixture of unrefined tridecanal (containing an estimated amount of about 10% mixed dodecenes) and dodecene-1 was prepared and became a homogeneous (one phase) composition upon heating to 90° C. The homogeneous composition was separated into six equal samples and various amounts of water or dodecene-1 or both water and dodecene-1 were added to said samples as shown in Table 5 below and each sample was allowed to cool about 25° C. and phase separate into two liquid layers, a non-polar top phase and a polar bottom phase. Analysis of each liquid layer of each sample by the same GC, HPLC and ASS methods described in Example 1 was conducted and the results are given in the Table 5 below.

TABLE 5

| | | Weight Percentage of Each Component in Each Liquid Layer | | | | | |
| --- | --- | --- | --- | --- | --- | --- | --- |
| Sample | Additive | Rhodium | Free TPPMS-NA | Water | NMP | Dodecene-1 | Tridecanal Aldehyde |
| 1. | [10% Water] | | | | | | |
| | Non-Polar Phase | 13.4 | 0.25 | 16.1 | 12.6 | 100 | 97.0 |

TABLE 5-continued

| Sample | Additive | Weight Percentage of Each Component in Each Liquid Layer | | | | | |
|---|---|---|---|---|---|---|---|
| | | Rhodium | Free TPPMS-NA | Water | NMP | Dodecene-1 | Tridecanal Aldehyde |
| 2. | Polar Phase [30% Water] | 86.6 | 99.75 | 83.9 | 87.3 | 0 | 2.1 |
| | Non-Polar Phase | 1.5 | 0.05 | 6.8 | 3.8 | 100 | 99.2 |
| 3. | Polar Phase [20% Dodecene-1] | 98.5 | 99.95 | 93.2 | 96.2 | 0 | 0.8 |
| | Non-Polar Phase | 14.4 | 2.6 | 47.7 | 54 | 96.6 | 93.5 |
| 4. | Polar Phase [40% Dodecene-1] | 85.6 | 97.4 | 52.6 | 46 | 3.4 | 6.5 |
| | Non-Polar Phase | 11.2 | 0.50 | 49.9 | 49.7 | 97.7 | 95.0 |
| 5. | Polar Phase [60% Dodecene-1] | 88.8 | 99.50 | 50.1 | 50.3 | 2.3 | 5.0 |
| | Non-Polar Phase | 0.9 | 0.35 | 55.3 | 47.4 | 98.0 | 95.5 |
| 6. | Polar Phase [10% Water and 20% Dodecene-1] | 99.1 | 99.65 | 44.7 | 52.6 | 2.0 | 4.5 |
| | Non-Polar Phase | 0.4 | 0.01 | 4.9 | 4.5 | 94 | 97.8 |
| | Polar Phase | 99.6 | 99.99 | 95.1 | 95.5 | 6 | 2.2 |

The above phase separation results illustrate that the addition of water alone is better than the addition of dodecene-1, while the addition of both water and dodecene-1 resulted in a synergistic phase separation of all the main components of the treated liquid composition.

EXAMPLE 6

In a continuous catalyst liquid recycle manner, dodecene-1 was hydroformylated for four days as follows.

The liquid recycle reactor system employed contained two 2.8 liter stainless steel stirred tank reactors, connected in series, each containing a vertically mounted agitator and a circular tubular sparger near the bottom of the reactor for feeding the syn gas. The sparger contained a plurality of holes of sufficient size to provide the desired gas flow into the liquid body. Reactor 1 and Reactor 2 were heated by electrical heaters. Both reactors contained internal cooling coils for controlling the reaction temperature. Reactors 1 and 2 were connected via a line to transfer any unreacted gases from Reactor 1 to Reactor 2 and were further connected via a line so that a portion of the liquid reaction solution containing aldehyde product and catalyst from Reactor 1 could be pumped into Reactor 2 wherein the unreacted olefin of Reactor 1 is further hydroformylated in Reactor 2.

Each reactor also contained a pneumatic liquid level controller for automatic control of the liquid levels in the reactors. Reactor 1 further contained a line for introducing the liquid olefin using a metering pump, and a line for introducing syn gas through the sparger, while make syn gas was added to reactor 2 via the same transfer line carrying the unreacted syn gas from Reactor 1. Reactor 2 also contained a blow-off vent for removal of the unreacted gases.

A line (e.g., line 4 of Fig.) for removal of the hydroformylation reaction product composition from Reactor 2 was connected to a mixer (e.g., 102 of Fig.) consisting of a series of five cocurrent stainless steel spray columns. Water and a non-polar hydrocarbon were added to said line (e.g., via lines 3 and 12 of Fig.) upstream from the first spray column and the hydroformylation reaction product composition along with the added water and added non-polar hydrocarbon thoroughly mixed by spraying the combined liquids into the top of the first spray column and then spraying the combined liquids removed from the bottom of the first spray column into the bottom of the second spray column. Since the liquids were removed from the bottom of the first spray column, the lighter liquid phase tended to accumulate in the first spray column. Hence in the first spray column the lighter non-polar phase was continuous with the heavier polar phase dispersed in it. In the second spray column the combined liquids were removed from the top, resulting in a reversal of the phases (i.e., the heavy polar phase being continuous and the lighter non-polar phase being dispersed in it) and sprayed into the top of third spray column, and this alternating spray procedure continued through the last two spray columns operated in series. The thoroughly mixed hydroformylation reaction product composition—water—non-polar hydrocarbon mixture obtained from the bottom of the fifth spray column was conveyed through a line (e.g., via line 4a of Fig.) to a glass decanter (e.g., 103 of Fig.) consisting of a verticle column of about 2" diameter and 7.5" long, said line extending about half way up the decanter so that the liquid mixture of non-polar and polar components could be introduced to the decanter near the normal liquid-liquid interface level of said components. The interface level in the decanter was determined by a capacitance type probe which senses the level of the polar phase which has a higher electrical conductivity than the non-polar phase. The decanter interface level was controlled by pumping the polar phase (e.g., via line 6 of Fig.) from the bottom of the decanter to a vaporizer (e.g., 105 of Fig.). The decanter pressure was controlled by a back regulator which allowed the crude non-polar phase to flow from the top of the decanter and be conveyed (e.g., via line 5 of Fig.) to a counter-current liquid-liquid extractor (e.g. 104 of Fig.). The decanter was operated at ambient temperature and the temperature of the liquids inside the decanter measured with a thermo couple located inside the decanter.

Said extractor consisted of a laboratory scale Karr glass tube extraction column. Agitation in the column was accomplished by moving a plate stack up and down (about a one inch stroke) inside the glass tube. The agitator plate stack consisted of 60 flat agitator plates spaced one inch apart attached to a central shaft. The agitation rate could be controlled by varying the rpm of a variable speed drive motor and/or adjusting the drive mechanism. At either end of the verticle extraction column was a glass decanter vessel. The liquid-liquid interface in the extractor was sensed by a capacitance type probe identical to the decanter probe and the interface controlled in the lower glass decanter. As a result, the continuous phase in the extraction column was the less dense non-polar phase with the more dense polar phase dispersed in it. The interface could be controlled by varying the feed rate of water to the extraction column. Water was fed to the top of the extraction column (e.g., via line 13 of Fig.) from a continuous polar organic solubilizing agent-water distillation column (e.g., 106 of Fig.) by a piston type metering pump. The pump flow rate was automatically controlled by a variable speed drive motor. The aqueous polar liquid collected from the bottom of the extraction column was continuously pumped through a line (e.g., via line 10 of Fig.) split by a solenoid valve and a timer and a portion of the aqueous polar liquid sent (e.g., via line 12 of Fig.) to the hydroformylation reaction product composition to be treated and the remaining aqueous polar liquid sent (e.g., via line 11 of Fig.) to the polar organic solubilizing agent-water distillation column (e.g., 106 of Fig.) mentioned above.

The extraction column pressure was controlled by a back regulator which allowed the non-polar aldehyde product containing phase to flow (e.g., via line 9 of Fig.) from the top of the extractor to an aldehyde product collection drum. The liquid-liquid extractor was operated at ambient temperature and the temperature of the liquids inside the extractor measured with a thermocouple located inside the extractor.

A dilute aqueous solution of fresh TPPMS-Na ligand, when employed, (e.g. line 15 of Fig.) was continuously fed to the water of e.g. line 13 of the Figure from the distillation column (e.g. 106 of Fig.) prior to entering the extraction column (e.g. 104 of Fig.).

The polar liquid phase obtained from the bottom of the decanter (e.g., 103 of Fig.) was pumped to a water vaporizer (e.g., 105 of Fig.) for vaporization of the water contained in said polar phase. The non-aqueous rhodium-monosulfonated tertiary phosphine metal salt ligand complex containing liquid obtained from said vaporizer along with the non-aqueous organic solubilizing agent liquid obtained from the distillation column (e.g., 106 of Fig.) were both recycled to the first reactor.

The hydroformylation reaction was conducted by charging from one liter (about 960 grams) of a catalyst precursor solution of rhodium dicarbonyl acetylacetonate (about 300 ppm rhodium), about 10 wt. % of 3-(diphenylphosphine)-benzenesulfonic acid, sodium salt ligand (TPPMS-Na) having the formula

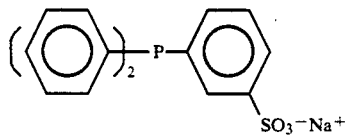

(about 94 mole equivalents of ligand per mole of rhodium), about 40 wt. % of unrefined tridecanal (containing an estimated amount of about 10 wt. % of mixed dodecenes) and as the polar organic solubilizing agent for the rhodium-monosulfonated tertiary phosphine metal salt ligand complex catalyst and the free monosulfonated tertiary phosphine metal salt ligand, about 50 wt. % of N-methyl pyrrolidone (NMP), to each reactor. In addition, about 300 of said catalyst precursor solution mixed with about 100 ml. of deionized water (to cause phase separation was charged to the decanter (e.g., 103 of Fig.). The reboiling flask on the distillation column (e.g., 106 Fig.) was filled with about 160 ml. of NMP and the overhead receiving flask filled with about one liter of deionized water. The vaporizer recycle system (pump and lines) was also filled with NMP. The extraction column of the extractor (e.g., 104 of Fig.) was filled with enough water to obtain a 50 percent level reading on the interface probe. Said probe was located on the bottom of the column. Hence, the polar phase was dispersed in the continuous non-polar phase. Initially, the extraction column was not filled with aldehyde, but after start-up began to fill with aldehyde as it was removed from the decanter. Once all of the solutions were charged to the system, the valves on the pump suction lines were shut to isolate each part of the system and all of the temperature controllers turned on to heat the system. The reactors were purged with nitrogen.

The system was then starting up in the following manner. The vaporizer (e.g., 105 of Fig.) and the distillation column (e.g., 106 of Fig.) were started up first. Once the vaporizer and distillation column reboiler temperatures were established at 130°-140° C. and 140°-150° C. respectively, the vaporizer recycle and water recycle pumps were started (suction valves opened and pumps turned on). The non-aqueous rhodium-monosulfonated tertiary phosphine metal salt ligand complex containing liquid discharge obtained from the vaporizer however was recycled to the top of the vaporizer, rather than the first reactor. Similarly, the water recycle obtained form the distillation column was recycled to the top of the vaporizer, rather than the extraction column. Both pumps were set on a manual control flow rate of 0.5-1.5 liters per hour. The vacuum pump was then started and the operating pressure of the vaporizer and distillation column was established at about 170 mm Hg. (absolute). Operating in this total recycle mode allowed the temperature profiles in the vaporizer and distillation column to be established without offsetting the rest of the system.

Once the operation of the distillation column had been established, the water flow throughout the system was started. The liquid-liquid extractor pump was started and set at a desired flow of about 0.5 to 1.5 liters per hour and was used to independently establish the water recycle flow throughout the system. Once the desired flow was obtained (by feeding the pump from a feed funnel) the suction of the pump was switched into the system (fed from the extraction column). As the water level in the extraction column decreased, the discharge from the water recycle pump of the distillation column was switched from recycling to the vaporizer to feeding (e.g., via line 13 of Fig.) water to the extraction column of the liquid-liquid extractor. The extraction column interface controller was switched to automatic control to control the interface level by varying the amount of water pumped to the extraction column by the water recycle pump.

The three way splitter valve and time for the aqueous polar phase obtained from the extractor (e.g., in line 10 of Fig.) was then turned on to split the water flow from the extractor pump discharge between that sent to the hydroformylation reaction product composition to be treated (e.g., via line 12 of Fig.) and that sent to the distillation column (e.g., via line 11 of Fig.). In general 75% of the aqueous polar liquid obtained from the extractor was sent to the distillation column and 25% was sent to the hydroformylation reaction product solution to be treated. Due to the addition of water, the interface level in the decanter (e.g., 103 of Fig.) began to increase. The decanter pump was started (suction valve opened and pump turned on) and the decanter interface level controller set on automatic control. The aqueous polar phase obtained from the decanter pump was sent to the vaporizer (e.g., via line 6 of Fig.).

Hence in this mode of operation water was recycled through the distillation column, decanter and vaporizer in a closed loop, all on automatic control without affecting the hydroformylation reactors.

Once stable operation of the aldehyde product recovery from the extractor (e.g., via line 9 of Fig.) and the non-aqueous, rhodium-monosulfonated tertiary phosphine metal salt ligand complex containing liquid recycle system of the vaporizer (e.g., via line 8 of Fig.) was achieved, olefin (dodecene-1) and syn gas (CO & $H_2$) feeds were started to the reactors. Both reactor pumps were started and both reactor liquid level controllers were set on automatic control. When the reactor liquid level in each reactor reached the setpoint the second reactor pump began pumping its hydroformylation reaction medium comprising aldehyde, the rhodium-monosulfonated tertiary phosphine metal salt ligand complex catalyst, the free monosulfonated tertiary phosphine metal salt ligand and the polar organic solubilizing agent for said complex catalyst and said free ligand to the cocurrent mixer (e.g., 102 of Fig. via line 4 of Fig.) and when the vaporizer was operating at full temperature (as indicated by a thermocouple located in the vapor space of the separator), the non-aqueous rhodium-monosulfonated tertiary phosphine metal salt ligand complex liquid discharge obtained from the vaporizer (e.g., via line 8 of Fig.) was switched from being recycled to the top of the vaporizer to being recycled to the first reactor.

Dodecene-1 was then pumped to the hydroformylation reaction product composition to be treated (e.g. via line 3 of Fig.) as the added non-polar hydrocarbon compound to assist in the phase separation of the aldehyde from said product composition. TPPMS-Na ligand was added (e.g. via line 15 of Fig.) to the water fed (e.g. via line 13 of Fig.) to the liquid-liquid extractor (e.g. 102 of Fig.) at this time.

The phase separated non-polar aldehyde containing liquid was removed from the decanter (e.g. 103 of Fig.) via an overflow (e.g. line 4a of Fig.) through a back pressure regulator and conveyed to the bottom of the liquid-liquid extraction column (e.g. 104 of Fig.). The extraction column slowly filled with aldehyde and the desired aldehyde product was obtained as it overflowed through a back pressure regulator into an aldehyde collection drum (e.g., via line 9 of Fig.).

The hydroformylation of dodecene-1 was carried out continuously for one day as a trial run to confirm and adjust mechanical performance of the apparatus assembly and after one day of operation, the reactors were briefly shut-down to discharge the hydroformylation reaction mediums from the reactors. The remainder of the phase separation and recovery systems however were kept operating using a close loop recycle for the liquid discharge from the vaporizer as described above. One liter of fresh catalyst precursor solution having the same ingredients and composition as described above was added to each reactor, heated, and the olefin and syn gas feeds were restarted. The non-aqueous rhodium-monosulfonated tertiary phosphine ligand complex containing liquid discharge from the vaporizer was then switched back to the first reactor. This procedure simplified the start up of the new run, but left some of the hydroformylation reaction product composition from the previous run in the system. However the amount of such composition left in the system was small compared to that amount in the reactors. In addition, the composition left in the system was essentially the same as that employed in the new start up thus minimizing any carry over effects from the previous run.

The hydroformylation of said dodecene-1 was then carried out continuously for four days after said restart.

After the data was collected on Day 3, sufficient rhodium in the form of rhodium dicarbonyl acetylacetonate was added to the reactors to increase the rhodium concentration from 300 to 520 ppm. A sufficient amount of the same TPPMS-Na ligand was also added to increase the catalyst reaction solution by about 3 wt. %. and no TPPMS-Na ligand was mixed with the water added to the extractor.

The hydroformylation reaction conditions as well as the mixer/decanter conditions and liquid-liquid extraction column conditions along with the results obtained from this experiment are given in Tables 6 and 7 below, (said information being keyed to the stream line numbers of the Figure drawing). During this experiment the ligand concentrations in both reactors and the other parts of the system were not measured. As a result all analyses in Table 7 below are reported on a ligand-free basis (i.e. normalized to equal 100% without including the amount of ligand present).

TABLE 6

| Days of Operation | 1 | 2 | 3 | 4 |
| --- | --- | --- | --- | --- |
| Olefin Feed, wt % | | | | |
| 1-Dodecene | 99.04 | 99.02 | 99.06 | 98.18 |
| 2-Dodecene + Dodecene | 0.96 | 0.98 | 0.94 | 1.82 |
| Reactor Conditions (Reactor 1/Reactor 2) | | | | |
| Temperature °C. | 90/90 | 90/90 | 90/90 | 90/90 |
| Pressure, psig | 95/79 | 95/77 | 95/79 | 95/79 |
| Liquid Volume, liters | 1/1 | 1/1 | 1/1 | 1/1 |
| CO Partial Pressure, psi | 30/21 | 24/16 | 14/6 | 18/15 |
| H2 Partial Pressure, psi | 77/70 | 83/73 | 93/84 | 90/75 |
| 1-Dodecene, wt % | 9.0/1.9 | 11.6/2.9 | 14.9/5.2 | 12.1/3.4 |
| 2-Dodecene, wt % | 0.9/1.1 | 1.1/1.4 | 1.1/1.6 | 1.2/1.5 |
| Rhodium, ppm | 300/300 | 300/300 | 300/300 | 520/520 |
| TPPMS-Na, wt % | 10/10 | 10/10 | 10/10 | 13/13 |
| NMP, wt % | 46.9/46.3 | 46.5/45.0 | 47.6/47.6 | 50.1/49.2 |
| Tridecanal Average Rate, gmole/l/hr | 1.20 | 1.18 | 1.13 | 1.18 |
| Tridecanal Linear/Branched Isomer Ratio | 4.04 | 4.62 | 5.25 | 5.09 |
| Mixer/Decanter Conditions | | | | |
| Temperature, °C. | 28 | 28 | 30 | 29 |
| Pressure, psig | 170 | 160 | 160 | 160 |

TABLE 6-continued

| Days of Operation | 1 | 2 | 3 | 4 |
|---|---|---|---|---|
| Water Feed Rate, ml/hr (#12) | 245 | 242 | 245 | 245 |
| 1-Dodecene Feed Rate, gms/hr (#3) | 183 | 183 | 181 | 181 |
| Extractor Conditions | | | | |
| Temperature, °C. | 28 | 26 | 29 | 28 |
| Pressure, psig | 10 | 10 | 10 | 10 |
| Agitator, strokes/min | 235 | 236 | 237 | 236 |
| Product Rate (non-polar phase) gms/hr (#9) | 741 | 746 | 835 | 852 |
| Water Tails (polar phase) Flowrate, ml/hr (#10) | 978 | 968 | 978 | 978 |
| TPPMS-Na Addition Rate, gms/hr of ligand (added to #13) | 0.0123 | 0.0123 | 0.1246 | none |

TABLE 7

| Days of Operation | 1 | 2 | 3 | 4 |
|---|---|---|---|---|
| Rhodium Concentrations, parts per billion | | | | |
| Reactor 2 (#4) | 300000 | 300000 | 300000 | 500000 |
| Decanter Upper (non-polar) Phase (#5) | 1500 | 2700 | 940 | 994 |
| Extractor Product (non-polar) Phase (#9) | 210 | 127 | 58 | 199 |
| Extractor Water Tails (polar phase) (#10) | 1050 | 465 | 472 | 517 |
| Extractor Water Feed (#13) | <10 | 12 | 13 | not measured |
| Water Concentrations, wt % | | | | |
| Reactor 2 (#4) | 3.74 | 3.75 | 1.74 | 2.01 |
| Decanter Upper (non-polar) Phase (#5) | 4.00 | 3.73 | 2.90 | 3.24 |
| Decanter Lower (polar) Phase (#6) | 26.8 | 26.9 | 26.2 | not measured |
| Extractor Product (non-polar phase) (#9) | 4.02 | 4.80 | 5.28 | 4.67 |
| Extractor Water Tails (polar phase) (#10) | 95.5 | 94.7 | 94.6 | 93.2 |
| NMP Concentrations, wt % | | | | |
| Reactor 2 (#4) | 46.3 | 45.0 | 47.6 | 49.2 |
| Decanter Upper (non-polar) phase (#5) | 5.55 | 3.82 | 3.97 | 4.06 |
| Decanter Lower (polar) phase (#6) | 70.2 | 70.5 | 71.3 | not measured |
| Extractor Product (non-polar phase) (#9) | 0.013 | 0.013 | 0.014 | 0.013 |
| Extractor Water Tails (polar phase) (#10) | 4.46 | 5.14 | 5.33 | 6.70 |
| Extractor Water Feed (#13) | 0.000 | 0.018 | 0.000 | 0.022 |
| Tridecanal Concentrations, wt % | | | | |
| Reactor 2 (#4) | 42.4 | 42.5 | 39.6 | 38.7 |
| Decanter Upper (non-polar) Phase (#5) | 61.2 | 59.7 | 58.2 | 58.8 |
| Decanter Lower (polar) Phase (#6) | 0.34 | 0.31 | 0.33 | not measured |
| Extractor Product (non-polar phase) (#9) | 64.2 | 62.2 | 59.3 | 60.8 |
| Extractor Water Tails (polar phase) (#10) | 0.01 | 0.01 | 0.00 | 0.00 |
| Dodecene + Dodecane Concentrations, wt % | | | | |
| Reactor #2 (#4) | 5.06 | 6.43 | 8.38 | 6.86 |
| Decanter Upper (non-polar) Phase (#5) | 27.9 | 31.4 | 33.8 | 32.7 |
| Decanter Lower (polar) Phase (#6) | 0.02 | 0.03 | 0.04 | not measured |
| Extractor Product (non-polar phase) (#9) | 30.2 | 31.6 | 34.2 | 33.2 |
| Extractor Water Tails (polar phase) (#10) | 0.00 | 0.00 | 0.00 | 0.00 |

The above results illustrate the excellent over all phase separation of aldehyde product from the rhodium-phosphorus complex and N-methyl pyrrolidone solubilizing agent achieved in a continuous liquid catalyst recycle non-aqueous hydroformylation operation by adding water and a non-polar hydrocarbon (i.e. dodecene) to the non-aqueous hydroformylation reaction product of Reactor 2.

EXAMPLE 7

A non-aqueous hydroformylation reaction product solution was simulated by preparing a liquid mixture containing about 0.0151 grams of rhodium dicarbonyl acetylacetonate complex (about 300 ppm rhodium), about 2.8 grams of TPPMS-Na, i.e., the same phosphine ligand shown employed in Example 1 (the mole ratio of said ligand to rhodium being about 130:1), about 6.06 grams of N-methylpyrrolidone (NMP) as the polar organic solubilizing agent, and about 11.36 grams of heptanal aldehyde. One half of said liquid mixture which was a homogeneous (one phase) solution at ambient temperature (about 25° C.) was mixed with about 1 gram of water and 2 grams of hexane (non-polar hydrocarbon additive) which caused the phase separation of two liquid layers, a non-polar phase and a polar phase, upon settling at ambient temperature (about 25° C.). The other half of said solution was mixed with about 1° gram of water and 2 grams of nonane (non-polar hydrocarbon additive) which also caused the phase separation into two liquid layers, a non-polar phase and a polar phase, upon settling at ambient temperature (about 25° C.). The compositions of both phase separated liquid layers in each sample were analyzed by the same GC, HPLC and AAS methods described in Example 1 and the weight percentages of each component in each liquid layer are given in Table 8 below.

TABLE 8

| | | Weight Percentage of Each Component in Each Liquid Layer | | | | |
|---|---|---|---|---|---|---|
| Sample | Additive | Rhodium | Free TPPMS-NA | NMP | Heptanal | Hydrocarbon |
| 1. | Water-Hexane | | | | | |
| | Non-Polar Phase | <0.3[a] | 1.1 | 23.6 | 89.6 | 98.3 |
| | Polar Phase | >99.7 | 98.9 | 76.4 | 10.4 | 1.7 |
| 2. | Water-Nonane | | | | | |
| | Non-Polar Phase | <0.2[a] | 0.3 | 10.8 | 79.7 | 97.1 |
| | Polar Phase | >99.8 | 99.7 | 89.2 | 20.3 | 2.9 |

[a]Rhodium in Non-Polar Phase was below the detection limit of the AAS analysis method.

The above results illustrate good overall phase separation of the aldehyde from the rhodium, free ligand and the organic solubilizing agent when both water and a non-polar hydrocarbon are added to the liquid composition starting material.

EXAMPLE 8

A non-aqueous hydroformylation reaction product solution was simulated by preparing a liquid mixture containing about 0.0151 grams of rhodium dicarbonyl acetylacetonate complex (about 300 ppm rhodium), about 2.8 grams of TPPMS-Na, i.e., the same phosphine ligand shown employed in Example 1 (the mole ratio of said ligand to rhodium being about 130:1), about 8.02 grams of N-methylpyrrolidone (NMP) as the polar organic solubilizing agent, and about 9.2 grams of undecanal aldehyde. Said liquid mixture formed two liquid layers at ambient temperature (about 25° C.) but exists as one homogeneous phase at 90° C. One half of said homogeneous (one phase) solution was mixed with about 1 gram of water and 2 grams of hexane (non-polar hydrocarbon additive) at 90° C. and the treated solution allowed to cool to about 25° C. wherein it phase separated into two liquid layers, a non-polar phase and a polar phase, upon settling. The other half of said treated solution was mixed with about 1 gram of water and 2 grams of nonane (non-polar hydrocarbon additive) in the same manner and also allowed to cool to about 25° C. wherein it too phase separated into two liquid layers, a non-polar phase and a polar phase upon settling. The composition of both phase separated liquid layers in each sample were analyzed by the same GC, HPLC and AAS methods described in Example 1 and the weight percentages of each component in each liquid layer are given in Table 9 below.

TABLE 9

| | | Weight Percentage of Each Component in Each Liquid Layer | | | | |
|---|---|---|---|---|---|---|
| Sample | Additive | Rhodium | Free TPPMS-NA | NMP | Undecanal | Hydrocarbon |
| 1. | Water-Hexane | | | | | |
| | Non-Polar Phase | <0.3[a] | 0.4 | 34.6 | 94.6 | 97.6 |
| | Polar Phase | >99.7 | 99.6 | 65.4 | 5.4 | 2.4 |
| 2. | Water-Nonane | | | | | |
| | Non-Polar Phase | 1.0 | 0.5 | 23.2 | 95.7 | 97.9 |
| | Polar Phase | 99.0 | 99.5 | 76.8 | 4.3 | 2.1 |

[a]Rhodium in Non-Polar Phase was below the detection limit of the AAS analysis method.

The above results illustrate very good overall phase separation of the aldehyde for the rhodium, free ligand and the organic solubilizing agent when both water and a non-polar hydrocarbon are added to the liquid composition starting material.

EXAMPLE 9

The continuous catalyst liquid recycle experiment outlined in Example 6 was repeated using the same apparatus with the following modificatons and exceptions.

1-Hexene was fed to the hydroformylation reaction medium to produce heptanal instead of 1-dodecene to produce tridecanal.

Two liters (about 1986 grams) of a nonaqueous, single organic phase catalyst precursor solution of rhodium dicarbonyl acetylacetonate (about 360 ppm rhodium), about 15 wt. % of 3-(diphenylphosphine)-benzenesulfonic acid, sodium salt ligand (TPPMS-Na) having the same formula as shown in Example 6, which contained a small amount of water (about 14 wt. %) as a result of being recrystallized from water, the mole equivalents of ligand employed per mole of rhodium being about 118 to 1; about 37 wt. % of unrefined heptanal (containing an estimated amount of about 4 wt. % of mixed hexenes) and as the polar organic solubilizing agent for the rhodium-monosulfonated tertiary phosphine metal salt ligand complex catalyst and the free monosulfonated tertiary phosphine metal salt ligand, about 45 wt. % of N-methylpyrrolidone (NMP), to each reactor.

A degassing vessel was added in the decanter non-polar phase outlet line before entering the bottom of the extraction column. The vessel consisted of a ½ inch outer diameter piece of tubing mounted vertically. The non-polar liquid phase was introduced to the top of the vessel and nitrogen was sparged through the liquid at the bottom of the vessel to remove dissolved and entrained gases (hydrogen and carbon monoxide) from the product before entering the extraction column. The liquid level in the vessel was sensed with a differential pressure cell and automatically controlled by a motor valve which allowed the degassed aldehyde to flow to the base of the extraction column. The aldehyde was removed from the bottom of the degassing vessel. Gas was removed from the top of the vessel through a back-pressure regulator which was used to control the degassing vessel, decanter and mixer pressure. The temperature of the degassing vessel was automatically controlled at 55° C. with electric resistance heaters wrapped around the outside of the vessel.

A second vaporizer was added to the system to improve catalyst drying before returning it to the reactor. The vaporizers were operated in series. Catalyst from the decanter was introduced to the top of the upper vaporizer. The liquid tails stream from the upper vaporizer flowed by gravity to the top of lower vaporizer for further drying. The liquid tails stream from the lower vaporizer was pumped to the first reactor. The lower vaporizer was operated at a higher temperature to more completely dry the recycled catalyst solution. The vapor streams from both vaporizers were fed to the water/NMP distillation column. The liquid tails stream from the water/NMP distillation column was also fed to the top of the lower vaporizer to more completely dry it, rather than directly recycling it directly to the first reactor.

In this example the entire system was started up in the same manner as outlined in Example 6 with fresh catalyst (i.e., no trial run to confirm and adjust mechanism performance of the apparatus). Also during this example no TPPMS-Na ligand was added (e.g., via line 15 of Fig.) to the water fed (e.g. via line 13 of Fig.) to the liquid-liquid extractor (e.g. 104 of Fig.).

The hydroformylation of said 1-hexene was then carried out continuously for 17 days. During the experiment the concentration of NMP in the reactors was adjusted as desired by controlling the amount of NMP being recycled to the reactors (e.g. via line 14 of Fig.). For example at the end of day 1 the concentration had been adjusted to a more preferred weight percent of about 30 to 35 by interrupting and collecting about 572 grams of NMP from said recycle line, shown as line 14 of the Figure, the excess amount of NMP being unnecessary for solubilizing the complex catalyst and free ligand and maintaining a single, non-aqueous organic phase hydroformylation reaction medium in the reactors.

The hydroformylation reaction conditions as well as the mixer/decanter conditions and liquid-liquid extraction column conditions along with the results obtained from this experiment are given in Tables 10 and 11 below, (said information being keyed to the stream line numbers of the Figure drawing). Moreover during this example the TPPMS-Na ligand concentration was measured and hence all analyses are reported on a basis including the ligand concentration.

TABLE 10

| Days of Operation | 1 | 8 | 17 |
|---|---|---|---|
| Olefin Feed, wt % | | | |
| 1-Hexene | 99.44 | 99.44 | 99.58 |
| 2-Hexene + Hexane | 0.27 | 0.27 | 0.08 |
| Reactor Conditions (Reactor 1/Reactor 2) | | | |
| Temperature, °C. | 90/90 | 90/100 | 90/90 |
| Pressure, psig | 99/86 | 99/86 | 98/86 |
| Liquid Volume, liters | 2/2 | 2/2 | 2/2 |
| CO Partial Pressure, psi | 1/6 | 42/29 | 33/22 |
| H2 Partial Pressure, psi | 109/92 | 70/70 | 79/78 |
| 1-Hexene, wt % | 4.6/2.4 | 5.0/0.8 | 4.6/1.3 |
| 2-Hexene, wt % | 3.8/3.4 | 1.5/1.4 | 1.4/1.4 |
| Rhodium, ppm | 289/280 | 284/297 | 295/263 |
| TPPMS-Na, wt % | 14/20 | 13/13 | 14/12 |
| NMP, wt % | 37/36 | 31/30 | 34/32 |
| Heptanal Average Rate, gmole/l/hr | 0.86 | 1.06 | 0.98 |
| Heptanal Linear/Branched Isomer Ratio | 24.2 | 5.51 | 5.76 |
| Mixer/Decanter Conditions | | | |
| Temperature, °C. | 30 | 29 | 30 |
| Pressure, psig | 10 | 9 | 11 |
| Water Feed Rate, ml/hr (#12) | 376 | 504 | 503 |
| 1-Hexene Feed Rate, gms/hr (#3) | 0 | 0 | 0 |
| Extraction Column Conditions | | | |
| Temperature, °C. | 29 | 30 | 30 |
| Pressure, psig | 5 | 3 | 3 |
| Agitator, strokes/min | 136 | 144 | 140 |
| Extractor Product Flowrate (non-polar phase), gms/hr (#9) | 447 | 510 | 478 |
| Extractor Water Tails Flowrate (polar phase), ml/hr (#10) | 501 | 504 | 503 |

TABLE 11

| Days of Operation | 1 | 8 | 17 |
|---|---|---|---|
| Rhodium Concentrations, Parts per Billion | | | |
| Reactor 2 (#4) | 280000 | 297000 | 263000 |
| Decanter Upper (non-polar) Phase (#5) | 121 | 179 | 53 |
| Decanter Lower (polar) Phase (#6) | 335000 | 210200 | 278000 |
| Extractor Product (non-polar phase) (#9) | 245 | 231 | 201 |
| Extractor Water Tails (polar phase) (#10) | 783 | 123 | 1421 |
| Extractor Water Feed (#13) | <10 | <10 | <10 |
| TPPMS-Na Concentrations, ppm | | | |
| Reactor 2 (#4) | 200000 | 130000 | 120000 |
| Decanter Upper (non-polar) Phase (#5) | 220 | 60 | 470 |
| Decanter Lower (polar) Phase (#6) | 250000 | 130000 | 115000 |
| Extractor Product (non-polar phase) (#9) | 90 | 20 | 50 |
| Extractor Water Tails (polar phase) (#10) | 1920 | 2700 | 1920 |
| Extractor Water Feed (#13) | 30 | 20 | 30 |
| Water Concentrations, wt % | | | |
| Reactor 2 (#4) | 0.98 | 1.45 | 2.08 |
| Decanter Upper (non-polar) Phase (#5) | 1.16 | 1.68 | 1.18 |
| Decanter Lower (polar) Phase (#6) | 40.3 | 55.8 | 47.9 |
| Extractor Product (non-polar phase) (#9) | 0.68 | 0.86 | 0.89 |
| Extractor Water Tails (polar phase) (#10) | 89.6 | 94.4 | 94.3 |
| NMP Concentrations, wt % | | | |
| Reactor 2 (#4) | 35.6 | 30.1 | 32.4 |
| Decanter Upper (non-polar) Phase (#5) | 7.43 | 4.79 | 5.15 |
| Decanter Lower (polar) Phase (#6) | 41.0 | 28.7 | 47.9 |
| Extractor Product (non-polar phase) (#9) | 0.003 | 0.006 | 0.000 |
| Extractor Water Tails (polar phase) (#10) | 9.77 | 5.00 | 5.44 |
| Extractor Water Feed (#13) | 0.057 | 0.091 | 0.000 |
| Heptanal Concentrations, wt % | | | |
| Reactor 2 (#4) | 38.9 | 46.3 | 48.2 |

TABLE 11-continued

| Days of Operation | 1 | 8 | 17 |
|---|---|---|---|
| Decanter Upper (non-polar) Phase (#5) | 78.5 | 89.1 | 87.8 |
| Decanter Lower (polar) Phase (#6) | 2.91 | 2.27 | 2.55 |
| Extractor Product (non-polar phase) (#9) | 87.4 | 94.9 | 93.4 |
| Extractor Water Tails (polar phase) (#10) | 0.44 | 0.21 | 0.21 |
| Extractor Water Feed (#13) | 0.72 | 0.10 | 0.07 |
| Hexene + Hexane Concentrations, wt % | | | |
| Reactor 2 (#4) | 8.69 | 6.79 | 3.03 |
| Decanter Upper (non-polar) Phase (#5) | 12.2 | 4.49 | 5.48 |
| Decanter Lower (polar) Phase (#6) | 0.09 | 0.02 | 0.04 |
| Extractor Product (non-polar phase) (#9) | 10.9 | 3.79 | 5.33 |
| Extractor Water Tails (polar phase) (#10) | 0.00 | 0.00 | 0.00 |
| Extractor Water Feed (#13) | 0.02 | 0.00 | 0.06 |

The above results illustrate the excellent over all phase separation of aldehyde product from the rhodium-phosphorus complex, the free phosphorus ligand and N-methyl pyrrolidone solubilizing agent achieved in a continuous liquid catalyst recycle non-aqueous hydroformylation operation by adding water to the non-aqueous hydroformylation reaction product of Reactor 2.

EXAMPLE 10

The continuous catalyst liquid recycle experiment outlined in Example 9 was repeated using the same apparatus and 4-(diphenylphosphino)-butylsulfonate-sodium salt (DPBS-Na) as the ionic phosphine ligand along with the following additional modifications and exceptions.

1-Decene was fed to the hydroformylation reaction medium to produce undecanal instead of 1-hexane to product heptanal.

Two liters (about 1650 grams) of a nonaqueous, single phase catalyst precursor solution of rhodium dicarbonyl acetylacetonate (about 824 ppm rhodium), about 4.88 wt. % of DPBS-Na, the mole equivalents of ligand employed per mole of rhodium being about 17.7 to 1; about 51.5 wt. % of 1-decene and as the polar organic solubilizing agent of the rhodium-monosulfonated tertiary phosphine metal salt ligand complex catalyst and the free monosulfonated tertiary phosphine metal salt ligand, about 43.4 wt. % of N-methylpyrrolidone (NMP), was split into two equal portions and one portion was charged to each reactor. Initially, after the reactors had been heated to reaction temperature, only hydrogen and carbon monoxide were fed to the reactors to convert the 1-decene initially charged to the reactors to undecanal. After most of the 1-decene had been converted to undecanal, the 1-decene feed to the first reactor was established. Other flows were then established in the system, as described in Example 9. As a result, the concentrated catalyst solution in the reactors was distributed throughout the rest of the system, resulting in the reactor catalyst concentrations summarized in Table 12.

The degassing vessel, described in Example 9, was removed from the decanter non-polar phase outlet line. The decanter non-polar phase outlet line (stream #5) was fed directly to the bottom of the extraction column (#104). The degassing vessel (which had been moved to line #4a) was fed the mixture of water, hydrocarbon and catalyst from the mixers (#102). The degassed liquid from the degassing vessel was fed to the decanter (#103). The degassing vessel was operated at ambient temperature and nitrogen was not sparged through the bottom of the degassing vessel.

An additional mechanically agitated catalyst/water/hydrocarbon mixer was added after the previously described static mixers (#102). The mixture of catalyst, water, undecanal and hydrocarbon from the static mixers was fed to the bottom of the mechanical agitator. The mixture was removed from the top of the mechanical mixer and was fed to the degassing vessel described above. The mechanical mixer contained about 50 ml of liquid.

The polar catalyst containing phase (stream #6) from the decanter (#103) was fed to the reboiler of the distillation column (#106) instead of the vaporizer separator (#105). The tails stream from the reboiler (stream #14) was fed to the vaporizer separator (#105) for return to the oxo reactors (#101) via stream #8.

An adsorption bed consisting of a glass pipe about 2 inches in diameter and about 2 feet high was added to the apparatus. The pipe was filled with about 1 liter of powdered silica gel (ICN Adsorbentien, manufactured by ICN Biomedicals GmbH) and was mounted vertically in the apparatus. Product from the extraction column (stream #9) was continuously pumped into the bottom of the adsorption bed and was removed from the top of the bed after it had passed through the silica gel. The bed was operated at ambient temperature and the outlet of the bed was operated at ambient pressure. As the product from the extraction column passed through the bed, the rhodium and ligand remaining in the product was adsorbed by the bed. As a result, rhodium and ligand began to accumulate in the bed eventually resulting in a high pressure drop across the bed (>30 psi) or resulting in the breakthrough of rhodium or ligand in the product from the bed. This generally took 1 to 3 days to occur. At that time, extractor product (stream #9) was diverted away from the adsorption bed to a similar but smaller second adsorption bed (~250 ml of silica gel). Rhodium and ligand was recovered from the 1 liter bed by backflushing it (feeding liquid to the top of the bed and removing it from the bottom) with about 1 liter of polar solvent such as NMP followed by backflushing it with about 1 liter of non-polar 1-decene. Extractor product (stream #9) was then diverted back to the bottom of the 1 liter adsorption bed and the smaller adsorption bed was backflushed using the same procedure, but using only about 250 ml of polar solvent f(NMP) followed by about 250 ml of the non-polar 1-decene. All of the backflushes from the beds were composited and vaporized under vacuum (~10 mmHg) at ~95° C. to remove all of the water, NMP and 1-decene. The resulting dry mixture of rhodium and ligand was re-dissolved in water and returned to the reboiler of the hydroformylation apparatus (#106) in order to reintroduce the rhodium and ligand into the oxo reactor (#101) via reboiler tails stream #14.

The hydroformylation of said 1-decene was then carried out continuously for 15 days. The hydroformylation reaction conditions as well as the mixer/decanter conditions and liquid-liquid extraction column conditions along with the results obtained from this experiment are given in Tables 12 and 13 below, (said information being keyed to the stream line numbers of the Figure drawing).

TABLE 12

| Days of Operation | 1 | 7 | 15 |
|---|---|---|---|
| Olefin Feed, wt % | | | |
| 1-Decene | 98.55 | 98.20 | 98.36 |
| 2-Decene + Decane | 0.78 | 0.89 | 1.00 |
| Reactor Conditions (Reactor 1/Reactor 2) | | | |
| Temperature, °C. | 110/110 | 110/110 | 110/110 |
| Pressure, psig | 106/94 | 107/96 | 106/96 |
| CO Partial Pressure, psi | 18/16 | 30/20 | 30/21 |
| H2 Partial Pressure, psi | 100/90 | 90/88 | 90/88 |
| 1-Decene, wt % | 11.5/2.4 | 10.3/2.3 | 12.9/3.8 |
| 2-Decene, wt % | 2.5/2.9 | 1.6/1.7 | 1.6/1.9 |
| Rhodium, ppm | 484/446 | 347/405 | 305/296 |
| DPBS-Na, wt % | 2.8/2.6 | 2.0/2.1 | 2.4/2.4 |
| NMP, wt % | 35.7/35.5 | 40.9/40.9 | 41.0/40.3 |
| Undecanal Average Rate, gmole/1/hr | 1.05 | 1.02 | 1.14 |
| Undecanal Linear/Branched Isomer Ratio | 13.45 | 6.75 | 7.61 |
| Mixer/Decanter Conditions | | | |
| Temperature, °C. | 28 | 27 | 30 |
| Pressure, psig | 2.5 | 2.5 | 2.5 |
| Water Feed Rate, ml/hr (#12) | 258 | 330 | 364 |
| 1-Decene Feed Rate, gms/hr (#3) | none | none | none |
| Extraction Column Conditions | | | |
| Temperature, °C. | 31 | 40 | 40 |
| Pressure, psig | 0.5 | 0.5 | 0.5 |
| Agitator, strokes/min | 135 | 134 | 126 |
| Extractor Product Flowrate (non-polar phase), gms/hr (#9) | 416 | 388 | 449 |
| Extractor Water Tails Flowrate (polar phase), ml/hr (#10) | 262 | 335 | 370 |
| DPBS-Na Addition Rate to Top of Column, gms/hr of ligand (#13) | none | none | none |
| Adsorption Bed Results | | | |
| Rhodium concentration in product leaving the bed, ppb | <20 | <20 | <20 |
| Ligand concentration in product leaving the bed, ppm | <1 | <1 | <1 |

TABLE 13

| Days of Operation | 1 | 7 | 15 |
|---|---|---|---|
| Water Concentrations, wt % | | | |
| Reactor 2 (#4) | 0.53 | 0.52 | 0.44 |
| Decanter Upper (non-polar) Phase (#5) | 4.42 | 3.52 | 3.47 |
| Decanter Lower (polar) Phase (#6) | 44.5 | 48.4 | 46.4 |
| Extractor Product (non-polar phase) (#9) | not measured | 0.71 | 3.17 |
| Extractor Water Tails (polar phase) (#10) | 91.6 | 93.7 | 95.0 |
| NMP Concentrations, wt % | | | |
| Reactor 2 (#4) | 35.5 | 40.9 | 40.3 |
| Decanter Upper (non-polar) Phase (#5) | 4.42 | 3.52 | 3.47 |
| Decanter Lower (polar) Phase (#6) | 51.6 | 48.9 | 50.3 |
| Extractor Product (non-polar phase) (#9) | 0.354 | 0.043 | 0.154 |
| Extractor Water Tails (polar phase) (#10) | 8.29 | 6.21 | 4.90 |
| Extractor Water Feed (#13) | 0.000 | 0.000 | 0.000 |
| Undecanal Concentrations, wt % | | | |
| Reactor 2 (#4) | 53.3 | 50.2 | 48.8 |
| Decanter Upper (non-polar) Phase (#5) | 82.5 | 85.7 | 82.0 |
| Decanter Lower (polar) Phase (#6) | 0.20 | 0.18 | 0.06 |
| Extractor Product (non-polar phase) (#9) | 85.3 | 88.9 | 80.8 |
| Extractor Water Tails (polar phase) (#10) | 0.05 | 0.00 | 0.00 |
| Decene + Decane Concentrations, wt % | | | |
| Reactor 2 (#4) | 7.59 | 5.62 | 7.41 |
| Decanter Upper (non-polar) Phase (#5) | 11.71 | 9.52 | 12.20 |
| Decanter Lower (polar) Phase (#6) | 0.00 | 0.00 | 0.00 |
| Extractor Product (non-polar phase) (#9) | 12.1 | 10.0 | 13.0 |
| Extractor Water Tails (polar phase) (#10) | 0.00 | 0.00 | 0.10 |

During the 15 day experiment, no scrambling of the DPBS-Na ligand was observed in the oxo reactor. Also during the experiment, both rhodium and DPBS-Na were removed to below detectable limits (20 ppb and 1 ppm, respectively) in the aldehyde product leaving the silica gel adsorption bed.

The above results illustrate the excellent ligand and catalyst stability during the experiment and also illustrate the excellent over all phase separation of the aldehyde product from the rhodium-phosphorus complex, the free phosphorus ligand and N-methyl pyrrolidone solubilizing agent achieved in a continuous liquid catalyst recycle non-aqueous hydroformylation reaction product of Reactor 2.

Various modifications and variations of this invention will be obvious to a worker skilled in the art and it is to be understood that such modifications and variations are to be included within the purview of this application and the spirit and scope of the appended claims.

What is claimed is:

1. A process for separating aldehyde from a non-aqueous hydroformylation reaction product composition comprising an aldehyde containing from 7 to 31 carbon atoms, a rhodium-phosphorus ligand complex, free phosphorus ligand, and an organic solubilizing agent for said complex and said free ligand, wherein the phosphorus ligand of said complex and said free phosphorus ligand is an ionically charged phosphorus ligand having the formula:

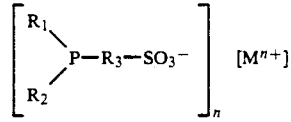

wherein $R_1$ and $R_2$ each individually represent a radical containing from 1 to 30 carbon atoms selected from the class consisting of alkyl, aryl, alkaryl, aralkyl and alicyclic radicals; wherein $R_3$ represents a divalent alkylene radical having from 2 to 12 carbon atoms or a divalent 1,3-phenylene radical; wherein M represents a metal cation selected from the group consisting of alkali and alkaline earth metals; and wherein n has a value of 1 or 2 corresponding to the valance of the particular metal cation represented by M, said process comprising (1) mixing said non-aqueous composition with from about 2 to about 60 percent by weight of added water and from 0 to about 60 percent by weight of an added non-polar hydrocarbon compound, said amounts of added water and added non-polar hydrocarbon compound being based on the total weight of said non-aqueous composition, and by phase separation forming a non-polar phase consisting essentially of aldehyde and the added non-polar hydrocarbon compound when employed, and a liquid polar phase consisting essentially of the added water, the rhodium-phosphorus complex, the free phosphorus ligand and the organic solubilizing agent for said complex and said free ligand; with the proviso that the amount of added water employed or the sum amount of added water and added non-polar hydrocarbon employed is at least sufficient to provide phase separation of at least about 70 weight percent of the aldehyde contained in said non-aqueous composition from at least about 90 weight percent of the rhodium-phosphorus complex calculated as rhodium metal also contained in said non-aqueous composition, and (2) recovering said non-polar phase from said polar phase.

2. A process as defined in claim 1, wherein the organic solubilizing agent is a polar organic liquid having molecular weight of less than 250 and a Hildebrand solubility value of at least 10, or mixtures of such liquids.

3. A process as defined in claim 2, wherein the polar organic solubilizing agent is selected from the group consisting of amides, sulfoxides, sulfones, and mixtures thereof.

4. A process as defined in claim 2, wherein the amount of added water employed or the sum amount of added water and added non-polar hydrocarbon compound employed and referred to in the proviso clause is at least sufficient to provide phase separation of at least about 70 weight percent of the aldehyde contained in said non-aqueous composition from at least about 95 weight percent of the rhodium-phosphorus complex calculate as rhodium metal and at least about 95 weight percent of the free phosphorus ligand also contained in said non-aqueous composition.

5. A process as defined in claim 2, wherein the amount of added water employed or the sum amount of added water and added non-polar hydrocarbon compound employed and referred to in the proviso clause is at least sufficient to provide phase separation of at least about 70 weight percent of the aldehyde contained in said non-aqueous composition from at least about 95 weight percent of the rhodium-phosphorus complex calculated as rhodium metal, at least about 95 weight percent of the free phosphorus ligand and at least 75 weight percent of the polar organic solubilizing agent for said complex and said free ligand also contained in said non-aqueous composition.

6. A process as defined in claim 2, wherein $R_3$ is a divalent alkylene radical.

7. A process as defined in claim 6, wherein $R_1$ and $R_2$ each individually represent a phenyl or cyclohexyl radical and wherein $R_3$ is a divalent 1,3-propylene or 1,4-butylene radical.

8. A process as defined in claim 2, wherein $R_3$ is a divalent 1,3-phenylene radical.

9. A process as defined in claim 8, wherein $R_1$ and $R_2$ are each individually selected from the group consisting of alkyl radicals having from 1 to 20 carbon atoms, aryl radicals having from 6 to 12 carbon atoms and alicylic radicals having from 5 to 12 carbon atoms.

10. A process as defined in claim 9, wherein $R_1$ and $R_2$ are each individually selected from the group consisting of branched chain alkyl radicals having from 3 to 9 carbon atoms, phenyl and cyclohexyl radicals.

11. A process as defined in claim 10, wherein $R_1$ and $R_2$ are both phenyl radicals, wherein n is 1 and M is an alkali metal.

12. A process as defined in claim 3, wherein the organic solubilizing agent is N-methyl pyrrolidone.

13. A process as defined in claim 2, wherein the added non-polar hydrocarbon compound is a saturated straight chain alkane containing from 6 to 30 carbon atoms.

14. A process as defined in claim 2 wherein step (1) consists essentially of mixing said non-aqueous composition with only added water.

15. A process as defined in claim 14, wherein the amount of added water employed in said mixing step is from about 2 to about 30 percent by weight based on the total weight of said non-aqueous composition.

16. A process as defined in claim 2, wherein step (1) consists essentially of mixing said non-aqueous composition with both added water and an added non-polar hydrocarbon compound.

17. A process as defined in claim 16, wherein the amount of added water employed in said mixing step is from about 2 to 30 percent by weight and the amount of added non-polar hydrocarbon compound employed in said mixing step is from about 2 to 30 percent by weight, said amounts of added water and added non-polar hydrocarbon compound being based on the total weight of said non-aqueous composition.

18. A process as defined in claim 9, wherein the polar organic solubilizing agent is selected from the group consisting of amides, sulfoxides, sulfones, and mixtures thereof; wherein the added non-polar hydrocarbon is a saturated straight chain alkane containing from 6 to 30 carbon atoms; and wherein the amount of added water employed or the sum amount of added water and added non-polar hydrocarbon compound employed and referred to in the proviso clause is at least sufficient to provide phase separation of at least about 70 weight percent of the aldehyde contained in said non-aqueous composition from at least about 95 weight percent of the rhodium-phosphorus complex calculated as rhodium metal, at least about 95 weight percent of the free phosphorus ligand and at least 75 weight percent of the polar organic solubilizing agent for said complex and said free ligand also contained in said non-aqueous composition.

19. A process as defined in claim 18, wherein $R_1$ and $R_2$ are each individually selected from the group consisting of branched chain alkyl radicals having from 3 to 9 carbon atoms, phenyl and cyclohexyl radicals.

20. A process as defined in claim 19, wherein $R_1$ and $R_2$ are both phenyl radicals, wherein n is 1 and M is an alkali metal.

21. A process as defined in claim 20, wherein M is sodium.

22. A process as defined in claim 21, wherein the polar organic solubilizing agent is N-methyl pyrrolidone.

23. A process as defined in claim 22, wherein the sum amount of added water and non-polar hydrocarbon compound employed and referred to in the proviso clause is at least sufficient to provide phase separation of at least about 90 weight percent of the aldehyde contained in the non-aqueous composition from at least about 98 weight percent of the rhodium-phosphorous complex calculated as rhodium metal, at least about 98 weight percent of the free phosphorus ligand and at least 85 weight percent of the polar organic solubilizing agent for said complex and said free ligand also contained in said non-aqueous composition.

24. A process as defined in claim 23 wherein step (1) consists essentially of mixing said non-aqueous composition with only added water.

25. A process as defined in claim 24, wherein the amount of added water employed in said mixing step is from about 2 to about 30 percent by weight based on the total weight of said non-aqueous composition.

26. A process as defined in claim 23, wherein step (1) consists essentially of mixing said non-aqueous composition with both added water and an added non-polar hydrocarbon compound.

27. A process as defined in claim 26, wherein the amount of added water employed in said mixing step is from about 2 to 30 percent by weight and the amount of added non-polar hydrocarbon compound employed in said mixing step is from about 2 to 30 percent by weight, said amounts of added water and added non-polar hydrocarbon compound being based on the total weight of said non-aqueous composition.

28. In a continuous liquid catalyst recycle, non-aqueous hydroformylation process for producing aldehydes which comprises hydroformylating an olefinic compound containing from 6 to 30 carbon atoms with carbon monoxide and hydrogen in the presence of a solubilized rhodium-monosulfonated tertiary phosphine metal salt ligand complex catalyst, solubilized free monosulfonated tertiary phosphine metal salt ligand and a polar organic solubilizing agent for said complex catalyst and said free ligand in a hydroformylation reactor, obtaining therefrom a non-aqueous hydroformylation reaction product composition comprising the aldehyde product containing from 7 to 31 carbon atoms, the rhodium-monosulfonated tertiary phosphine metal salt ligand complex, the free monosulfonated phosphine metal salt ligand and the polar organic solubilizing agent for said complex and said free ligand, separating and recovering aldehyde product from said non-aqueous composition and recycling the remaining rhodium-monosulfonated tertiary phosphine metal salt ligand complex containing liquid which also contains said free monosulfonated tertiary phosphine metal salt ligand and said polar organic solubilizing agent to the hydroformylation reactor after said separation of aldehyde product, the improvement comprising separating said aldehyde product from said non-aqueous hydroformylation reaction product composition by mixing said non-aqueous composition with from about 2 to about 60 percent by weight of added water and from 0 to 60 percent by weight of an added non-polar hydrocarbon compound, said amounts of added water and added non-polar hydrocarbon compound being based on the total weight of said non-aqueous composition, and by phase separation forming a liquid non-polar phase consisting essentially of aldehyde and the added non-polar hydrocarbon when employed, and a liquid polar phase consisting essentially of the added water, the rhodium-monosulfonated tertiary phosphine metal salt ligand complex, the free monosulfonated tertiary phosphine metal salt ligand and the polar organic solubilizing agent for said complex and said free ligand, recovering said non-polar phase from said polar phase, and recycling said polar phase after removal of the water to the hydroformylation reactor, with the proviso that the amount of added water employed or the sum amount of added water and added non-polar hydrocarbon employed is at least sufficient to provide phase separation of at least about 70 weight percent of the aldehyde contained in said non-aqueous composition from at least about 90 weight percent of the rhodium-monosulfonated. tertiary phosphine metal salt ligand complex calculated as rhodium metal also contained in said non-aqueous composition.

29. A process as defined in claim 28, wherein the polar organic solubilizing agent is selected from the group consisting of amides, sulfoxides, sulfones, and mixtures thereof; wherein the monosulfonated tertiary phosphine metal salt ligand of said complex and said free monosulfonated tertiary phosphine metal salt ligand is an ionically charged phosphorus ligand having the formula

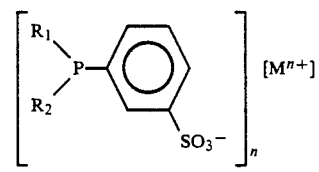

wherein $R_1$ and $R_2$ are each individually selected from the group consisting of alkyl radicals having from 1 to 20 carbon atoms, aryl radicals having from 6 to 12 carbon atoms and alicylic radicals having from 5 to 12 carbon atoms; wherein the added non-polar hydrocarbon is a saturated straight chain alkane containing from 6 to 30 carbon atoms; wherein M represents a metal cation selected from the group consisting of alkali and alkaline earth metals; wherein n has a value of 1 or 2 corresponding to the valance of the particular metal cation represented by M; and wherein the amount of added water employed or the sum amount of added water and added non-polar hydrocarbon compound employed and referred to in the proviso clause is at least sufficient to provide phase separation of at least about 70 weight percent of the aldehyde contained in said non-aqueous composition from at least about 95 weight percent of the rhodium-monosulfonated tertiary phosphorus metal salt complex calculated as rhodium metal, at least about 95 weight percent of the free monosulfonated tertiary phosphine metal salt ligand and at least about 75 weight percent of the polar organic solubilizing agent for said complex and said free ligand also contained in said non-aqueous composition.

30. A process as defined in claim 29, wherein the organic solubilizing agent is N-methyl pyrrolidone; wherein $R_1$ and $R_2$ are both phenyl radicals; wherein n is 1 and wherein M is an alkali metal.

31. A process as defined in claim 30, wherein only added water is mixed with said non-aqueous composition.

32. A process as defined in claim 31, wherein the amount of added water employed in said mixing step is from about 2 to about 30 percent by weight based on the total weight of said non-aqueous composition.

33. A process as defined in claim 30, wherein both added water and an added non-polar hydrocarbon compound are mixed with said non-aqueous composition.

34. A process as defined in claim 33, wherein the amount of added water employed in said mixing step is from about 2 to 30 percent by weight and the amount of added non-polar hydrocarbon compound employed in said mixing step is from about 2 to 30 percent by weight, said amounts of added water and added non-polar hydrocarbon compound being based on the total weight of said non-aqueous composition.

35. A process as defined in claim 7, wherein $R_1$ and $R_2$ are phenyl radicals.

36. A process as defined in claim 7, wherein the phosphorus ligand is 3-(diphenylphosphino)propylsulfonate-sodium salt.

37. A process as defined in claim 7, wherein the phosphorus ligand is 4-(diphenylphosphino)butylsulfonate-sodium salt.

38. A process as defined in claim 7, wherein the organic solubilizing agent is a polar organic liquid having molecular weight of less than 250 and a Hildebrand solubility value of at least 10, or mixtures of such liquids and wherein the amount of added water employed or the sum amount of added water and added non-polar hydrocarbon employed is at least sufficient to provide phase separation at least about 95 weight percent of the rhodium-phosphorus complex calculated as rhodium metal contained in said non-aqueous composition.

39. A process as defined in claim 6, wherein droplets of a finely divided emulsion and/or micelles of the polar phase dispersed in the obtained non-polar aldehyde product phase are removed therefrom by passing said obtained non-polar aldehyde product phase through a carbonaceous or inorganic adsorbent bed.

40. A process as defined in claim 39, wherein the adsorbent bed is silica gel.

41. A process as defined in claim 40 wherein $R_1$ and $R_2$ are phenyl radicals.

42. A process as defined in claim 41, wherein the phosphorus ligand is 3-(diphenylphosphino)propylsulfonate-sodium salt.

43. A process as defined in claim 41, wherein the phosphorus ligand is 4-(diphenylphosphino)butylsulfonate-sodium salt.

44. A process as defined in claim 28, wherein the polar organic solubilizing agent is selected from the group consisting of amides, sulfoxides, sulfones, and mixtures thereof; wherein the monosulfonated tertiary phosphine metal salt ligand of said complex and said free monosulfonated tertiary phosphine metal salt ligand is an ionically charged phosphorous ligand having the formula

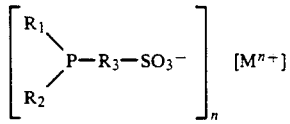

wherein $R_1$ and $R_2$ each individually represent a radical containing from 1 to 30 carbon atoms selected from the class consisting of alkyl, aryl, alkaryl, aralkyl and alicyclic radicals; wherein $R_3$ represents a divalent alkylene radical having from 2 to 12 carbon atoms; wherein M represents a metal cation selected from the group consisting of alkali and alkaline earth metal metals; and wherein n has a value of 1 to 2 corresponding to the valance of the particular metal cation represented by M.

45. A process as defined in claim 44, wherein $R_1$ and $R_2$ each individually represent a phenyl or cyclohexyl radical and wherein $R_3$ is a divalent 1,3-propylene or 1,4-butylene radical.

46. A process as defined in claim 45, wherein $R_1$ and $R_2$ are phenyl radicals.

47. A process as defined in claim 46, wherein the phosphorus ligand is 3-(diphenylphosphino)propylsulfonate-sodium salt.

48. A process as defined in claim 46, wherein the phosphorus ligand is 4-(diphenylphosphino)butylsulfonate-sodium salt.

49. A process as defined in claim 44, wherein droplets of a finely divided emulsion and/or micelles of the polar phase dispersed in the obtained non-polar aldehyde product phase are removed therefrom by passing said obtained non-polar aldehyde product phase through a carbonaceous or inorganic adsorbent bed.

50. A process as defined in claim 49, wherein the adsorbent bed is silica gel.

51. A process as defined in claim 50, wherein $R_1$ and $R_2$ are phenyl radicals.

52. A process as defined in claim 51, wherein the phosphorus ligand is 3-(diphenylphosphino)propylsulfonate-sodium salt.

53. A process as defined in claim 51, wherein the phosphorus ligand is 4-(diphenylphosphinobutyl)sulfonate-sodium salt.

54. A process as defined in claim 28, wherein the amount of added water employed or the sum amount of added water and added non-polar hydrocarbon employed is at least sufficient to provide phase separation at least about 95 weight percent of the rhodium-phosphorus complex calculated as rhodium metal contained in said non-aqueous composition.

55. A process for removing dispersed droplets of a finely divided emulsion and/or micelles of the polar phase contained in an non-polar aldehyde product phase, wherein said polar phase consists essentially of water, a rhodium-phosphorus ligand complex, free phosphorus ligand and a polar organic solubilizing agent for said complex and said free ligand, and wherein the ligand of said complex and said free ligand is ionically charged phosphorous ligand having the formula

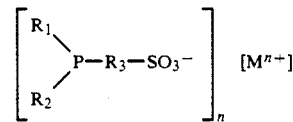

wherein $R_1$ and $R_2$ each individually represent a radical containing from 1 to 30 carbon atoms selected from the class consisting of alkyl, aryl, alkaryl, aralkyl and alicyclic radicals; wherein $R_3$ represents a divalent alkylene radical having from 2 to 12 carbon atoms; wherein M represents a metal cation selected from the group consisting of alkali and alkaline earth metals; and wherein n has a value of 1 or 2 corresponding to the valance of the particular metal cation represented by M, which comprises passing said non-polar aldehyde product phase through a carbonaceous or inorganic adsorbent bed.

56. A process as defined in claim 55, wherein the adsorbent bed is silica gel.

57. A process as defined in claim 56, wherein $R_1$ and $R_2$ are phenyl radicals.

58. A process as defined in claim 56, wherein the phosphorus ligand is 3-(diphenylphosphino)propylsulfonate-sodium salt.

59. A process as defined in claim 57, wherein the phosphorus ligand is 4-(diphenylphosphinobutyl)sulfonate-sodium salt.

* * * * *